(12) United States Patent
Eriksen et al.

(10) Patent No.: US 11,248,257 B2
(45) Date of Patent: Feb. 15, 2022

(54) METHOD OF IMMOBILIZING A NUCLEIC ACID PROBE TO A SOLID SUPPORT

(71) Applicant: Zoetis Services LLC, Parsippany, NJ (US)

(72) Inventors: Johan Eriksen, Birkerød (DK); Wai Hoe Chin, Dyssegård (DK); Martin Jensen Søe, Farum (DK); Martin Heller, Farum (DK)

(73) Assignee: ZOETIS SERVICES LLC, Parsippany, NJ (US)

(*) Notice: Subject to any disclaimer, the term of this patent is extended or adjusted under 35 U.S.C. 154(b) by 159 days.

(21) Appl. No.: 16/111,856

(22) Filed: Aug. 24, 2018

(65) Prior Publication Data
US 2019/0078151 A1    Mar. 14, 2019

(30) Foreign Application Priority Data
Aug. 25, 2017 (DK) .................. PA 2017 00464

(51) Int. Cl.
*C12Q 1/6834* (2018.01)
*B01J 19/00* (2006.01)

(52) U.S. Cl.
CPC ........ *C12Q 1/6834* (2013.01); *B01J 19/0046* (2013.01); *B01J 2219/00576* (2013.01); *B01J 2219/00605* (2013.01); *B01J 2219/00711* (2013.01); *B01J 2219/00722* (2013.01); *C12Q 2537/143* (2013.01); *C12Q 2565/518* (2013.01)

(58) Field of Classification Search
None
See application file for complete search history.

(56) References Cited

U.S. PATENT DOCUMENTS

| | | | |
|---|---|---|---|
| 6,221,635 B1 | 4/2001 | Rovera et al. | |
| 6,238,866 B1 | 5/2001 | Yeh et al. | |
| 2003/0165876 A1 | 9/2003 | Blanche et al. | |
| 2008/0085839 A1* | 4/2008 | Klapproth | C12Q 1/6827 506/12 |
| 2011/0086776 A1 | 4/2011 | Jarrige-Le Prado et al. | |
| 2011/0319275 A1 | 12/2011 | Pierik et al. | |
| 2012/0016340 A1 | 1/2012 | Xu et al. | |
| 2014/0194306 A1 | 7/2014 | Andersen et al. | |

FOREIGN PATENT DOCUMENTS

| | | |
|---|---|---|
| CN | 102409101 A | 4/2012 |
| EP | 2334810 A1 | 6/2011 |
| KR | 20150039540 A | 4/2015 |
| WO | 8911548 A1 | 11/1989 |
| WO | 0077257 A1 | 12/2000 |
| WO | 02/083894 A1 | 10/2002 |
| WO | 02077274 A2 | 10/2002 |
| WO | 03008583 A2 | 1/2003 |
| WO | 2005040400 A2 | 5/2005 |
| WO | 2006029908 A1 | 3/2006 |
| WO | 2006089366 A1 | 8/2006 |
| WO | 2010038170 A1 | 4/2010 |
| WO | 2010038191 A1 | 4/2010 |
| WO | 2017133741 A1 | 8/2017 |

OTHER PUBLICATIONS

Gen Bank Accession No. CR184233 (Year: 2004).*
Gen Bank Accession No. AQ975625 (Year: 2000).*
Artisantg.com (webpage downloaded from the internet Dec. 31, 2020).*
Gen Bank Accession No. BY218981 (database entry 2002) (Year: 2002).*
Gen Bank Accession No. BB659433 (database entry 2001) (Year: 2001).*
Haukur G. et al."An inexpensive and simple method for thermally stable immobilization of DNA on an unmodified glass surface: UV linking of poly(T) 10-poly(C) 10-tagged DNA probes" BioTechniques, vol. 45, No. 3, Sep. 2008, pp. 261-271.
Sun Y. et al."Direct immobilization of DNA probes on non-modified plastics by UV irradiation and integration in microfluidic devices for rapid bioassay" Anal Bioanal Chem, 2012, vol. 402, pp. 741-748.
Saiki R. K. et al."Genetic analysis of amplified DNA with immobilized sequence-specific oligonucleotide probes" Proc. Natl. Acad. Sci. USA, vol. 86, Aug. 1989, pp. 6230-6234.
Steel A. B. et al. "Immobilization of Nucleic Acids at Solid Surfaces: Effect of Oligonucleotide Length on Layer Assembly" Biophysical Journal, vol. 79, No. 2, Aug. 2000, pp. 975-981.
Pierik A. et al."Immobilization of Oligonucleotides with Homo-oligomer Tails onto Amine-Functionalized Solid Substrates and the Effects on Hybridization" Analytical Chemistry. vol. 82, No. 4, Feb. 15, 2010, pp. 1191-1199.
Kova J."Surface Characterization of Polymers by XPS and SIMS Techniques" Materiali in tehnologije/Materials and technology,vol. 45, No. 3, 2011, pp. 191-197.
Search Report dated Mar. 9, 2018, by the DanishTrademark Office in Patent Application PA 2017 00464, 9 pages. (With Reply).
Hung, T. Q. et a."A novel lab-on-chip platform with integrated solid phase PGR and Supercritical Angle Fluorescence (SAF) microlens array for highly sensitive and multiplexed pathogen detection" Elsevier, Biosensors and Bioelectronics, vol. 90, 2017, pp. 217-223.
International Search Report and Written Opinion (Forms PCT/ISA/210 and PCT/ISA/237) dated Sep. 11, 2018, by the International Searching Authority in corresponding International Application No. PCT/DK2018/050207. (21 pages).

(Continued)

Primary Examiner — Christopher M Gross
(74) Attorney, Agent, or Firm — Buchanan Ingersoll & Rooney P.C.

(57) ABSTRACT

A nucleic acid probe, a method of immobilizing the nucleic acid probe to a solid support and the solid support including the immobilized probes using UV light. The nucleic acid probe includes a terminus anchor chain portion, and a capture portion wherein the terminus anchor chain portion includes a sequence of at least 18 nucleotides composed of stretches of up to 5 nucleotides of base type X with intermediate nucleotide(s) of base type Cytosine (C) and optionally one nucleotide of base type Guanine (G) or a sequence with at least 90% similarity thereto, wherein each base type X independently of each other designate base type Thymine (T) or base type Uracil (U).

24 Claims, 35 Drawing Sheets
Specification includes a Sequence Listing.

(56) References Cited

OTHER PUBLICATIONS

Chen, R. et al.: "Immobilization of aptamers onto unmodified glass surfaces for affordable biosensors", Proceedings of the SPIE, 2011, vol. 8034, XP009526928 (9 pages).
Supplementary European Search Report in corresponding European Application No. 18 848 995.9, dated Apr. 23, 2021 (3 pages).
European Search Opinion in corresponding European Application No. 18 848 995.9, dated Apr. 23, 2021 (5 pages).

* cited by examiner

Different lengths and configurations of
TC polytail

UV crosslink

Measure signal A, wash, and
measure signal B.
Comparison signal between A and B.

Washing

No washing

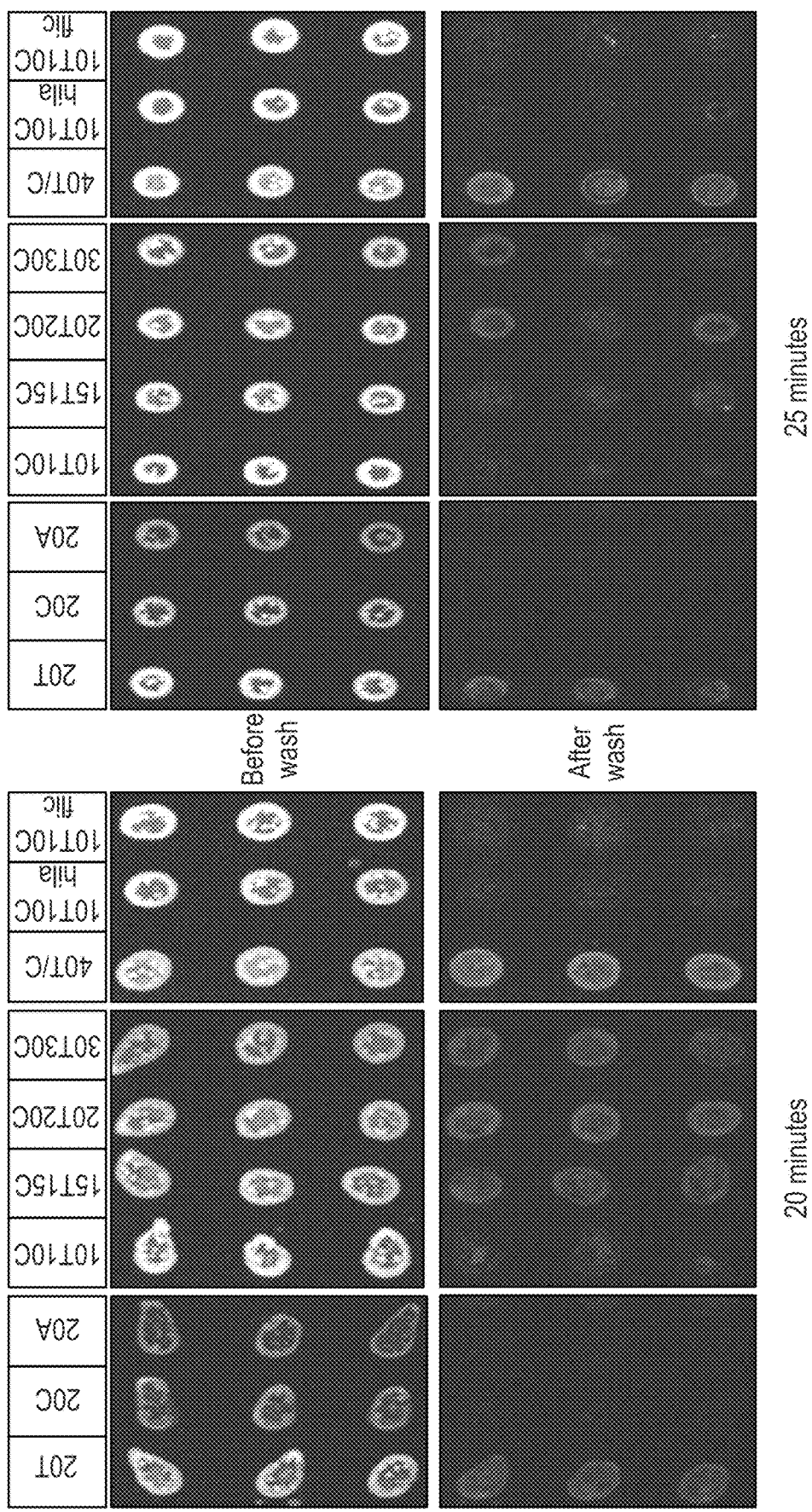

SECTION A-A

SECTION A-A

SECTION A-A

METHOD OF IMMOBILIZING A NUCLEIC ACID PROBE TO A SOLID SUPPORT

CROSS REFERENCE TO RELATED APPLICATION

The present application claims the benefit of Danish Application No. PA 2017 00464, filed on Aug. 25, 2017. The entire contents of Danish Application No. PA 2017 00464 are hereby incorporated herein by reference in their entirety.

TECHNICAL FIELD

The present invention generally relates to immobilizing of nucleic acid probes to solid substrates, such as a microfluidic cartridge. Such nucleic acid probes may advantageously be applied for capturing target components and/or for hybridization assay purposes.

BACKGROUND ART

Assay devices for use in the investigation and/or detection of biomolecules are very important tools. Different types of devices carrying immobilized probes for hybridization assay have been developed and marketed in recent years.

Several attempt for improving the assay devices and for immobilizing desired probes have been suggested. Some prior art methods comprises synthesizing a sequence of nucleotides directly onto a support structure. Other and more effective method comprises first providing a nucleic acid probe e.g. by isolating it from a natural source or by synthesizing.

A. B. Steel et al. DOI: http://dx.doi.org/10.1016/50006-3495(00)76351-X; "Immobilization of Nucleic Acids at Solid Surfaces: Effect of Oligonucleotide Length on Layer Assembly". Biophysical Journal Vol. 79, August 2000 p. 975-981 discloses a study of the effect of DNA length and the presence of an anchoring group on the assembly of pre-synthesized oligonucleotides at a gold surface. The study shows that thiol anchoring group strongly enhances oligonucleotide immobilization, but that the enhancement is reduced for longer strand lengths. For strands longer than 24 bases, the surface coverage begins to decrease notably with probe length.

Anke Pierik et al. DOI: 10.1021/ac902561w; "Immobilization of Oligonucleotides with Homo-oligomer Tails onto Amine-Functionalized Solid Substrates and the Effects on Hybridization". Anal. Chem., 2010, 82 (4), pp 1191-1199 discloses a study of photochemical (254 nm UV) DNA immobilization onto amine-functionalized substrates. It was concluded that short homo-oligomer sequences (tails) of uracils, thymines, and to a limited extent, guanines attached to a hybridization sequence improve immobilization. It was proposed that a possible mechanism explaining the grafting of these nucleotides to amine-functionalized substrates.

A similar immobilizing method is disclosed in EP2334810. The invention disclosed therein focuses on using longer wavelengths for immobilizing nucleic acids, namely 300-500 nm and it is considered that using such long wavelength light the risk of causing damages to nucleic acid molecules is reduced. The disclosed method comprises the steps of:
(a) providing a nucleic acid with a stretch of nucleotides of only one base type, wherein the stretch of nucleotides of only one base type is located at least at the 3' or 5' terminus of the nucleic acid; and
(b) immobilizing the nucleic acid on a solid support by crosslinking by light, wherein the crosslinking by light is performed at a wavelength of about 300-500 nm, preferably at a wavelength of 365 nm, wherein the stretch of nucleotides of only one base type has a length from about 7 to about 100 nucleotides, and the crosslinking is performed using an amount of energy ranging from about 0.5 Joule/cm$^2$ to about 10 Joule/cm$^2$.

DISCLOSURE OF THE INVENTION

The objective of the invention is to provide an alternative method of immobilizing of nucleic acid probes to solid substrates, which is simple and effective.

In an embodiment it is an objective to provide a method of immobilizing of nucleic acid probes to solid substrates wherein the substrate does not require pretreatment, such as pretreatment comprising amine-Functionalization or thiol functionalization of the solid support and preferably where the substrate is of thermoplastic and injected moldable material which does not require any surface functionalization after being produced by injection molding.

In an embodiment, it is an objective to provide a method of immobilizing of nucleic acid probes to solid substrates wherein the substrate does not require washing after the immobilization by UV light. Thereby the final device support carrying the immobilized probes can be produced at reduced cost.

The objective of the invention is to provide a probe comprising a terminus anchor chain portion for immobilizing the nucleic acid probe to a substrate with a high effectivity and wherein the substrate advantageously does not require pretreatment.

These objectives has been accomplished by the invention or embodiments thereof as defined in the claims and described herein below.

The invention provides a new and effective method of immobilizing a nucleic acid probe to a solid support. The inventors of the invention has found a novel anchoring change for immobilizing a nucleic acid probe to a solid support where the immobilization efficiency is surprisingly high and the risk of undesired damage to the nucleic acid probe is very low.

The method of immobilizing a nucleic acid probe to a solid support, the method comprises
- providing the nucleic acid probe to comprise a terminus anchor chain portion, and a capture portion
- applying the nucleic acid probe onto a surface of the solid support, and
- anchoring the anchor chain portion of the nucleic acid probe to the solid support by subjecting it to UV light.

The terminus anchor chain portion of the nucleic acid probe comprises a sequence of N nucleotides composed of stretches of nucleotides of base type X with intermediate nucleotide(s) of base type Cytosine (C)) and optionally one nucleotide of base type Guanine (G) or a sequence with at least 90% similarity thereto. The stretches of nucleotides of base type X independently of each other comprises from 1 to 5 nucleotides. N is at least 18 and each base type X independently of each other designate base type Thymine (T) or base type Uracil (U). In an embodiment, N is at least 20.

In an embodiment, the terminus anchor chain portion has at most 1 or is free of nucleotides of base type G.

Percent similarity is determined by counting the number n of nucleotides in the sequence of N nucleotides which differs from the composition of stretches from 1 to 5 nucleotides of base type X with intermediate nucleotide(s) of base type C and calculating the similarity percent 100*(N−n)/N.

The terms nucleotide(s) of a specific base type, such as of respective base type Cytosine (C), base type Thymine (T) or base type Uracil (U) are herein used to include nucleotides comprising the specific base type as well as chemical derivative thereof known to the person skilled in the art which is capable of interacting with a complementary base, including functionally equivalent derivatives or modifications thereof. The term "functionally equivalent" relates to the capability of the base to establish a non-covalent connection with a complementary base, which is chemically similar to the non-covalent connection of the nucleotide or base it is derived from. Such functionally equivalent or modified bases may still be able to perform a hybridization binding with a complementary base.

The terms "terminus anchor chain portion", "polytail" or merely "anchor change" are herein used interchangeable.

The term "target component" means any component which may be captured by and/or be synthesized at the capture portion e.g. by hybridization, primer extension or other reactions.

The terms "distal" and "proximal" should be interpreted in relation to the orientation of the optical transmitter device or any other device used in connection with minimally invasive surgery.

The term "about" is generally used to include what is within measurement uncertainties. When used in ranges the term "about" should herein be taken to mean that what is within measurement uncertainties is included in the range.

It should be emphasized that the term "comprises/comprising" when used herein is to be interpreted as an open term, i.e. it should be taken to specify the presence of specifically stated feature(s), such as element(s), unit(s), integer(s), step(s) component(s) and combination(s) thereof, but does not preclude the presence or addition of one or more other stated features.

Unless otherwise specified or clear from the context, the term "substantially" means that ordinary measurement uncertainties, or product variances and tolerances, whichever are larger, are comprised.

The term "essentially" should herein be taken to mean that variations which are practically irrelevant for the purpose in question are included.

Throughout the description or claims, the singular encompasses the plural unless otherwise specified or required by the context.

The phrase "an embodiment" should be interpreted to include examples of the invention comprising the feature(s) of the mentioned embodiment.

All features of the invention and embodiments of the invention as described herein, including ranges and preferred ranges, may be combined in various ways within the scope of the invention, unless there are specific reasons not to combine such features.

By providing the novel nucleic acid probe the inventors of the present invention has made a large and valuable contribution to the art of immobilizing nucleic acids to solid substrates. The method provided by the inventors has several very valuable advantages, which will be explained further below.

In an embodiment, the terminus anchor chain portion of the nucleic acid probe comprises said sequence of N nucleotides composed of stretches of nucleotides of base type X with intermediate nucleotide(s) of base type Cytosine (C). The combination of base type X and base type C has shown to be very advantageous for obtaining a high immobilization efficiency. Thus in an embodiment at least about 90%, such as at least about 95%, such as each of the N nucleotides are independently of each other of base type X or of base type C.

The stretches of nucleotides of base type X comprise at least one nucleotide of base type X for each stretch. The stretches of nucleotides of base type X may have equal or different length. In an embodiment, some, such as every second or every third of the stretches of nucleotides of base type X have a first length and some other, such as every second or every third stretches of nucleotides of base type X have a second longer length.

It has been found that where the nucleic acid probe comprises one or more stretches of nucleotide of base type X comprising 2-5 nucleotides the risk of detachment of probes, which give false negative, may be highly reduced.

Advantageously the sequence of N nucleotides comprises less than 10%, preferably less than 5% of nucleotides with purine nucleobases, such as 1 or zero nucleotides with purine nucleobases.

Nucleotides with purine nucleobases are Adenine (A) and Guanine (G). It has been found that nucleotides with purine nucleobases generally reduced the immobilization efficiency of the nucleic acid probe. It is believed that this may be because the high immobilization efficiency of the nucleic acid probe is caused by formation of covalent bonds by reactions at the C=C double bonds of pyrimidine. Thus, the nucleotides with purine nucleobases will not be bonded to the solid support by this reaction.

Advantageously the sequence of N nucleotides comprises exclusively nucleotides with pyrimidine nucleobases.

In an embodiment, the terminus anchor chain portion of the nucleic acid probe comprises a sequence of at least N nucleotides composed of stretches of from 2 to 5 nucleotides of base type X with intermediate nucleotide(s) of base type C.

The number N of nucleotide of the terminus anchor chain portion should advantageously not be too low because this may result in a too weak bonding between the terminus anchor chain portion and the solid support. However, it is also desired that the total number of nucleotide of the nucleic acid probe is not too high, since this may result in that the number of immobilized nucleic acid probes per area unit may be low and/or in that the nucleic acid probes may partly block for each other thereby resulting in a relatively weak immobilizing. Advantageously N is at least 26, such as at least 30, such as at least 34, such as at least 38, such as at least 40.

Generally, it is believed that increasing the number N of nucleotide of the terminus anchor chain to above 60 does not result in further increasing immobilization efficiency. In an embodiment, the number N of nucleotide of the terminus anchor chain is less than 50.

Advantageously the stretches of nucleotides of base type X independently of each other are separated by from 1-4 nucleotide(s) of base type C.

In an embodiment, the stretches of nucleotides of base type X are of equal length, preferably a length of 2 nucleotides of base type X, a length of 3 nucleotides of base type X or a length of 4 nucleotides of base type X.

It has been found that where the terminus anchor chain portion comprises a repetitive sub-sequence of nucleotide of base type X and nucleotide of base type C a very high immobilization efficiency may be obtained and the risk of detachment of immobilized nucleic acid probe is very low even when subjected to temperature shifts such as those provided in thermocycling processes such as the thermocycling applied in PCR (polymerase chain reaction) for amplification of DNA segments.

In a highly suitable embodiment, the sequence of N nucleotides comprises repeating sub-sequences of nucleotides of base types according to the formula $$(-(X)_Y-(C)_Z-)_M,$$

wherein Y is an integer from 1 to 5, Z is an integer from 1 to 5, Y≥Z and M is an integer from 4 to 20.

Advantageously Y is an integer from 2 to 5, Z is an integer from 1 to 4, Y>Z and M is an integer from 4 to 20.

In an embodiment Z=1. In an embodiment Z=2. In an embodiment Y=2 and M≥10, such as M≥12, such as M≥14. In an embodiment Y=3 and M≥6, such as M≥8, such as M≥10. In an embodiment Y=4 and M≥4, such as M≥6, such as M≥8.

In another highly suitable embodiment, the sequence of N nucleotides comprises repeating sub-sequences of nucleotides of base types according to the formula $$(-(X)_{Y2}-(C)_Z-(X)_{Y2}-)_M,$$

wherein $Y_2$ is an integer from 1 to 4, Z is an integer from 1 to 4, and M is an integer from 4 to 20.

Preferably, $Y_2$ is an integer from 2 to 3, Z is an integer from 1 to 3. In an embodiment $Y_2 \geq Z$, preferably $Y_2 > Z$. In an embodiment $Y_2=2$ and M≥10, such as M≥12, such as M≥14. In an embodiment $Y_2=3$ and M≥4, such as M≥6, such as M≥8.

It has been found that embodiments where the number of base type X is larger than the number of base type C are preferred for obtaining a very high and stable immobilization efficiency.

In an embodiment, the number of Y or $Y_2$ is larger than the number of Z, preferably the number of Y or $Y_2$ is at least twice the number of Z.

In an embodiment, the stretches of nucleotides of base type X are stretches of nucleotides of base type T.

In an embodiment, the stretches of nucleotides of base type X are stretches of nucleotides of base type U.

Since the bonding of the terminus anchor chain portion to the solid support is believed to be a bonding caused by formation of covalent linkages by reactions localized on the C=C double bonds of the pyrimidine it is believed that nucleotides of base type U will have a bonding efficiency corresponding to the bonding efficiency of nucleotides of base type T In an embodiment the stretches of nucleotides of base type X comprises both nucleotides of base type T and nucleotides of base type U, such as alternating nucleotides of base type T and nucleotides of base type U.

The sequence of N nucleotides of the terminus anchor may be located at either end of the nucleic acid probe. In an embodiment, the sequence of N nucleotides of the terminus anchor is located at the 5'-end. In an embodiment, the sequence of N nucleotides of the terminus anchor is located at the 3'-end.

In an embodiment the nucleic acid probe has a terminus anchor at both its 5'-end or at its 3'-end, wherein the sequence of N nucleotides at respective the 5'-end and the 3'-end may be equal or different from each other.

The capture portion of the nucleic acid probe may comprise DNA, RNA, PNA, CNA, HNA, LNA or ANA; an oligonucleotide thereof, a fraction thereof; or any combination thereof.

In an embodiment the capture portion comprises 2'-O-methyl RNA, which is a commonly used analogous of RNA, where a methyl group is added to the 2' hydroxyl of the ribose moiety of the nucleoside thereby forming a methoxy group.

The DNA may be in the form of, e.g. A-DNA, B-DNA or Z-DNA. The RNA may be in the form of, e.g. p-RNA, i.e. pyranosyl-RNA or structurally modified forms like hairpin RNA or a stem-loop RNA.

The term "PNA" means a peptide nucleic acid, which is an artificially synthesized polymer similar to DNA or RNA which is used in biological research and medical treatments, but which is not known to occur naturally. The PNA backbone may be composed of repeating N-(2-aminoethyl)-glycine units linked by peptide bonds.

The term "HNA" means a hexitol nucleic acid, i.e. a DNA analogues which is built up from standard nucleobases and a phosphorylated 1,5-anhydrohexitol backbone.

The term "LNA" means a locked nucleic acid. Typically, a locked nucleic acid is a modified and thus inaccessible RNA nucleotide. The ribose moiety of an LNA nucleotide may for example be modified with an extra bridge connecting the 2' and 4' carbons.

The term "ANA" means an arabinoic nucleic acid or derivatives thereof.

The term "CNA" means an aminocyclohexylethane acid nucleic acid. Furthermore, the term relates to a cyclopentane nucleic acid, i.e. a nucleic acid molecule comprising for example 2'-deoxycarbaguanosine.

In an embodiment, the capture portion of the nucleic acid probe may comprise a combination of any one of DNA, RNA, PNA, CNA, HNA, LNA and ANA or fractions thereof.

In an embodiment the capture portion of the nucleic acid probe the nucleic acid molecules as defined herein may be in the form of short oligonucleotides, long oligonucleotides or polynucleotides.

In an embodiment, the capture portion of the nucleic acid probe is single-stranded.

In an embodiment, the capture portion of the nucleic acid probe is double-stranded.

In an embodiment, the nucleic acid probe is obtained from a natural source or is fully or partly synthesized.

Generally it is desired that at least the terminus anchor chain portion of the nucleic acid probe is at least partly synthesized, preferably fully synthesized.

In an embodiment, the entire nucleic acid probe is single-stranded.

In an embodiment the nucleic acid probe is double-stranded in at least a part of its length, such as in a part of its capture portion.

The capture portion may in principle be any kind of moiety capable of capturing a target component.

In an embodiment, the capture portion comprises a primer, such as a primer adapted for primer extension. Primer extension is a technique used for example for mapping the 5' ends of RNA. Primer extension can for example be used to determine the start site of transcription.

In an embodiment, the capture portion comprises a hybridization chain portion comprising a sequence of nucleotides, such as a sequence of nucleotides adapted to hybridize to a complementary region of a target nucleic acid probe and/or adapted for performing a Polymerase Chain Reaction (PCR) assay. When the PCR is performed from a primer/probe immobilized to a solid support it may also be referred to as a solid-phase PCR or SP-PCR.

In an embodiment, the capture portion is adapted for annealing complementary target DNA with application such as microarray hybridization, PCR, LAMP, WGA (whole-genome amplification), HDA, Solid phase PCR.

Loop-mediated isothermal amplification (LAMP) uses 4-6 primers recognizing 6-8 distinct regions of target DNA. A strand-displacing DNA polymerase initiates synthesis and 2 of the primers form loop structures to facilitate subsequent rounds of amplification. LAMP is rapid, sensitive, and amplification is so extensive that the magnesium pyrophosphate produced during the reaction can be seen by eye, making LAMP well-suited for field diagnostics.

Strand displacement amplification (SDA) relies on a strand-displacing DNA polymerase, typically Bst DNA Polymerase, Large Fragment or Klenow Fragment (3'-5' exo-), to initiate at nicks created by a strand-limited restriction endonuclease or nicking enzyme at a site contained in a primer. The nicking site is regenerated with each polymerase displacement step, resulting in exponential amplification. SDA is typically used in clinical diagnostics.

Helicase-dependent amplification (HDA) employs the double-stranded DNA unwinding activity of a helicase to separate strands, enabling primer annealing and extension by a strand-displacing DNA polymerase. Like PCR, this system requires only two primers. HDA has been employed in several diagnostic devices and FDA-approved tests.

Nicking enzyme amplification reaction (NEAR) employs a strand-displacing DNA polymerase initiating at a nick created by a nicking enzyme, rapidly producing many short nucleic acids from the target sequence. This process is extremely rapid and sensitive, enabling detection of small target amounts in minutes. NEAR is commonly used for pathogen detection in clinical and biosafety applications.

Real-time polymerase chain reaction (Real-Time PCR), also known as quantitative polymerase chain reaction (qPCR), is a laboratory technique of molecular biology based on the polymerase chain reaction (PCR). It monitors the amplification of a targeted DNA molecule during the PCR, i.e. in real-time, and not at its end, as in conventional PCR.

Advantageously the capture portion comprises a chain of nucleotides up to about 200 nucleotides and preferably shorter. In an embodiment, the capture portion comprises a chain of nucleotides having from about 4 to about 100 nucleotides, such as from about 10 to about 50 nucleotides, such as from about 20 to about 30 nucleotides.

The capture portion may be directly linked to the terminus anchor chain portion.

In an embodiment the capture portion is linked to the terminus anchor chain portion via a spacer, such as an abasic spacer, such as a repetitive number of spacers.

Examples of spacers includes a Spacer C3, a PC (photocleavable) spacer, a Hexanediol spacer, a Spacer 9, a Spacer 18, a 1',2'-Dideoxyribose (dSpacer), and nucleotides (A, T, G, C) spacers.

A Spacer C3 is a three-carbon spacer that is used to incorporate a short spacer arm into an oligonucleotide. Spacer C3 can be incorporated in consecutive additions if a longer spacer is required. Spacer 9 is a triethylene glycol chain that is 9 atoms long (6 carbons+3 oxygens), and is used to incorporate a spacer arm into an oligonucleotide. Spacer 9 can be incorporated in consecutive additions whenever a longer spacer is required. Spacer 18 is a hexaethylene glycol chain that is 18 atoms long (12 carbons+6 oxygens), and is used to incorporate a long spacer arm into an oligonucleotide. Spacer 18 can be incorporated in consecutive additions whenever a longer spacer is required.

These and other suitable spacers may e.g. be purchased from Gene Link, Inc. NY, USA or Bio-Synthesis Inc. TX USA.

In an embodiment, the terminus anchor chain portion is located at the 5'-end or at the 3'-end of the nucleic acid probe and the capture portion H is located at the other one of the 5'-end and the 3'-end.

In an embodiment, the nucleic acid probe comprises a terminus anchor chain portion at both of the 5'-end and the 3'-end and the capture portion is located between the terminus anchor chain portions optionally with in-between spacer(s).

For certain applications, it is desired that the nucleic acid probe comprises a marker. In other application or in the same application the target component carries a marker. Where both carry a marker, it may be desired that the markers are different. The marker(s) may in principle be any kind of marker.

In an embodiment the nucleic acid probe comprises a marker, such as a radioactive marker or a fluorescent marker, such as a cyanine dye e.g. Cy3 (1,1'-bis(3-hydroxypropyl)-3,3,3',3'-tetramethylindocarbocyanine) or Cy5 (1,1'-bis(3-hydroxypropyl)-3,3,3',3'-tetramethylindodicarbocyanine).

Cyanine dyes are important chemical modifications of oligonucleotides exhibiting intensive and stable fluorescence at visible light wavelengths. Cyanine dyes have sharp absorption bands, high extinction coefficients, excellent resistance to photobleaching and make DNA and other oligomers highly fluorescent, so that even single molecules can be observe The nucleic acid probe may be deposited onto the surface of the solid support by any method such as spotting.

The terms "spotting" and "printing" are herein used interchangeable.

Advantageously the spotting comprises spotting of the nucleic acid probe in a solvent onto the surface of the solid substrate.

The spotting may e.g. be performed using a spotting robot and/or an inkjet printer which for example uses the same technology as computer printers to expel nanoliter to picoliter volume droplets of probe solution, instead of ink, onto the surface of the solid support. Alternatively, these probes can be applied with a pin directly onto a specific location on the surface of the solid support.

Advantageously the nucleic acid probe is deposited onto the solid support in a solvent. The optimal concentration of the nucleic acid probe in the solvent depends largely on the length of the nucleic acid probe. However, it has also been found that when using nucleic acid probes having the preferred terminus anchor chain portions as described above the concentration of the nucleic acid probe may be increased.

In an embodiment, the nucleic acid probe is spotted in the solvent in a concentration of up to 100 µM, such as in a concentration of from about 1 µM to about 80 µM, such as from about 3 µM to about 70 µM, such as from about 5 µM t about 60 µM. In an embodiment, the nucleic acid probe is spotted in the solvent in a concentration of up to about 800 ng/µL, such as from about 1 ng/µL to about 500 ng/µL.

The individual spots may e.g. have a volume of from about 0.1 nL to about 1 nL, such as from about 0.05 nL to about 1 nL, such as from about 0.1 nL to about 0.8 nL, such as from about 0.3 nL to about 0.6 nL.

Examples of suitable solvents includes SSC (saline sodium citrate), DMSO (dimethyl sulfoxide), NaHPO4 (Sodium phosphate dibasic), SDS (Sodium dodecyl sulfate) and NaOH (Sodium hydroxide). A further example includes Triton X-100 in combination with SSC.

After being spotted onto the solid support the nucleic acid probe is dried, e.g. by allowing it to dry. Thereafter the solid support comprising the nucleic acid probe is subjected to the UV treatment.

In practice, the solid support may be of any kind of materials or combination thereof. Advantageously the solid support is a polymer support or a glass support, preferably the support comprises polystyrene (PS), cyclic olefin copolymer (COC), polycarbonate (PC), Poly-methyl methacrylate (PMMA) or a mixture comprising one or more of the before mentioned polymers.

The solid support may be a layered support.

In a preferred embodiment, the solid support comprises or is of polystyrene (PS). Preferably, at least the surface of the solid support to which the nucleic acid probe is spotted is a PS surface. Generally, it is desired that the substrate is non-foamed, and has a generally low friction and smooth surface.

The solid support may advantageously be an injection molded solid support. The injection molded solid support may optionally be subjected to post-molding surface modification with oxygen rich plasma to introduce polar groups at the surface of the solid support. This may in particular be an advantage where the surface is adapted to a hydrophilic character.

Due to the immobilization efficiency of the nucleic acid it may not be required to make any pre-treatment or add any functional group to the solid support.

Thus in an embodiment the solid support surface is essentially free of one or more of amine groups, methylene groups, thiol groups, epoxy groups, diazo groups or amide groups, preferably the support surface is essentially free of all of amine groups, methylene groups, thiol groups, epoxy groups, diazo groups or amide groups.

The solid support may advantageously be or form part of a cartridge, an ELISA assay plate, a cuvette, a microplate or any combinations thereof.

Such assay devices are generally known and in principle, any of these may form the solid support.

In an embodiment, the solid support is or form part of a cartridge comprising a channel with a channel surface defining the channel, wherein the surface of the solid substrate forms at least a part of the channel surface.

In an embodiment, the channel comprises a reaction section and the method comprises immobilizing the nucleic acid probe to a surface within the reaction section of the channel. The reaction may be a length section of the channel.

In an embodiment, reaction section comprises at least one optical element. The optical element may advantageously be constructed to redirect and preferably collimate light emitted from a fluorescent marker (fluorophore) of or connected to the immobilized nucleic acid probe.

In an embodiment, the optical element comprises a lens structure and/or a supercritical angle fluorescence structure (SAF structure), the SAF structure preferably has a top surface and the method comprises immobilizing the nucleic acid probe to the top surface.

The optical element advantageously has a conical, frustum shape as described further below.

Advantageously the solid substrate is or form part of the test device described further below.

The solid support may advantageously be a microfluidic cartridge such as the microfluidic cartridge disclosed in WO17133741, which is hereby incorporated by reference. In an embodiment, the solid support is provided by the SAF structure(s) as disclosed in WO17133741 and the nucleic acid probe is immobilized to the top surface(s) of the SAF structure(s).

It has been found that the nucleic acid probe may be immobilized onto the solid support using a relative low dose of UV light, thereby ensuring that the risk of damaging the capture portion of the nucleic acid probe is relatively low or even avoided.

In an embodiment, the anchor chain portion of the nucleic acid is anchored to the solid support by subjecting it to UV light comprising wavelength in the range of from about 250 nm to 500 nm, preferably comprising wavelength of at least one of about 254 nm, about 265 nm and/or about 365 nm.

In an embodiment the anchor chain portion of the nucleic acid is anchored to the solid support by subjecting it to UV light using a very low amount of energy e.g. from, about 0.2 Joule/cm$^2$ to about 1 Joule/cm$^2$, such as about 0.3 Joule/cm$^2$ or more.

In an embodiment the anchor chain portion of the nucleic acid is anchored to the solid support by subjecting it to UV light using an amount of energy from about 0.4 Joule/cm$^2$ to about 15 Joule/cm$^2$, such as from about 1 Joule/cm$^2$ to about 10 Joule/cm$^2$, such as from about 1.5 Joule/cm$^2$ to about 6 Joule/cm$^2$, such as from about 1.6 Joule/cm$^2$ to about 3 Joule/cm$^2$, such as from about 1.7 Joule/cm$^2$ to about 2 Joule/cm$^2$.

In an embodiment the nucleic acid probe is immobilized by exposing the solid support carrying the spotted and dried nucleic acid probe to an UV illumination for at least 30 sec, such as for about 1 to about 8 minutes, such as from about 2 to about 6 minutes. The UV illumination may e.g. be provided by a UV emitter, such as a 3-12 W UV emitter, such as a 5-10 W UV emitter.

Only a small amount of the emitted UV light is reaching and affecting the nucleic acid probe. Thus, when calculating the amount of energy the solid support is subjected to per area unit the distance between the UV emitter and the solid support as well as the divergence of the beam emitted must be taken into consideration.

The invention also comprises a solid support comprising an immobilized nucleic acid probe obtained by the method disclosed above.

It is believed that Ultraviolet light induces the formation of covalent linkages by reactions localized on the C=C double bonds. The pyrimidine dimers are molecular lesions formed from lesions formed from thymine or cytosine bases in DNA via photochemical reactions. So theoretically, the damage of the DNA molecule itself actually create the bonding between probe and PS.

As explained above the terminus anchor chain portion of the nucleic acid probe results in an increased immobilization efficiency to the solid support such as a PS solid support. It is hypothesized that this is because UV light induces the formation of covalent linkages by reactions localized on the C=C double bonds. As shown in the examples below 42TTCCTT$^7$ (SEQ ID NO:22) polytail increased at least 18 folds immobilized efficiency as compare to 20T$^{10}$C$^{10}$ (SEQ ID NO:1) polytail. The naming of the polytails is as follows. The first number indicated the total length of the terminus anchor chain portion (polytail), the letters indicates the nucleotide types and the lifted number indicates the number of times the mentioned sequence of nucleotides is repeated.

The structure and bonding at the surface of the solid support may for example be examined using Surface Analysis by X-Ray Photoelectron Spectroscopy e.g. as described in "SURFACE CHARACTERIZATION OF POLYMERS BY XPS AND SIMS TECHNIQUES" by Janez Kova, Materials and technology 45 (2011) 3, 191-197.

The invention also comprises a nucleic acid probe as disclosed above.

The novel nucleic acid probe is capable of being immobilized to a solid support with an increased immobilization efficiency. The nucleic acid probe comprises a terminus anchor chain portion, and a capture portion, wherein the terminus anchor chain portion of the nucleic acid probe comprises a sequence of N nucleotides composed of stretches of nucleotides of base type X with intermediate nucleotide(s) of base type Cytosine (C) or a sequence with at least 90% similarity thereto, wherein the stretches of nucleotides of base type X independently of each other comprises from 2 to 5 nucleotides, wherein N is at least 18.

Preferred nucleic acid probes are as the nucleic acid probes described above.

A particularly preferred nucleic acid probe is a nucleic acid probe where the sequence of N nucleotides comprises repeating sub-sequences of nucleotides of base types according to the formula

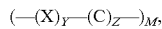

wherein Y, Z and M are as described above.

Another particularly preferred nucleic acid probe is a nucleic acid probe where the sequence of N nucleotides comprises repeating sub-sequences of nucleotides of base types according to the formula

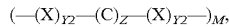

wherein $Y_2$, Z and M are as described above.

The invention also relates to a test device, which is suitable for use in the above described method.

The test device comprises a solid support which may be the solid support described above. The solid support comprises at least one supercritical angle fluorescence structure (SAF structure). The SAF structure has a conical, frustum shape with a frustum angle α, a top surface, a top diameter D and a height h.

The optimal frustum angle will normally be equal to the angle at which the fluorophore emits most of its light. This angle depends on two refractive indices of respective the SAF structure and the medium surrounding and in contact with the SAF structure i.e. air or the sample fluid, such as water or an aqueous fluid, which normally has a refractive index identical to water. It has been found that 60 degrees is best for the water/PS interface, whereas about 50 degrees is better for the air/PS interface.

The frustum angle α may for example be from about 40° to about 70°, such as from about 55° to about 65°, such as about 60°.

Generally it is desired that the frustum angle α is from about 30° to about 70°, such as from about 35 to about 65, such as from about 40° to about 60°, such as about 40° or about 60°. In an embodiment where the SAF structure(s) is of polystyrene and it is adapted for use with air surrounding and forming an air/polystyrene interface at the surface of the SAF structure the frustum angle α is advantageously from about 35° to about 55°. In an embodiment where the SAF structure(s) is of polystyrene and it is adapted for use with water (e.g. an aqueous sample fluid) surrounding and forming an air/polystyrene interface at the surface of the SAF structure the frustum angle α is advantageously from about 55° to about 65°.

In use the nucleic acid probe may be spotted onto the top surface of the SAF structure and dried e.g. as described elsewhere herein.

Advantageously the height h of the SAF structure is at least about 0.2 mm, such as from about 0.25 mm to about 0.5 mm, such as from about 0.3 mm to about 0.35 mm. It has been found that the height may be important in order to obtain an optimal signal.

Advantageously the top diameter is from about 0.05 mm to about 0.5 mm, such as from about 0.1 mm to about 0.3 mm. Generally, it is desired that the one or preferably more SAF structures are relatively small, because this allows more SAF structures on the same test device. Thereby several tests may be performed using one test device. However, where the top diameter is very small some of the nucleic acid probe may be spotted at the edge of the top surface or even beside the top surface. Hence a SAF structure with a very small top diameter e.g. where D is less than about 0.2, may have a low robustness for spotting.

It has been found that by ensuring that at least one SAF structure is relatively high compared to its top diameter the obtained read out signal has a very good intensity. Advantageously the SAF structure has a top diameter to height aspect ratio D/h, which is about 1.1 or less, such as about 1.05 or less, such as about 1 or less.

The solid support may preferably be a polymer support or a glass support. Preferably the support comprises polystyrene (PS), cyclic olefin copolymer (COC), polycarbonate (PC), Poly-methyl methacrylate (PMMA) or a mixture or a combination comprising one or more of the before mentioned polymers.

The support material may advantageously be transparent at least for the signal wavelength(s), which is expected to read out or use for excitation.

For example, Cy3 fluoresces greenish yellow (~550 nm excitation, ~570 nm emission), while Cy5 is fluorescent in the red region (~650 excitation, 670 nm emission).

In an embodiment, the support material is transparent for one or more wavelengths in and outside the visible range.

In an embodiment, the SAF structure is a PS SAF structure with an aspect ratio D/h, which is about 1.1 or less.

In an embodiment, the top surface of at least one SAF structure has a top surface recess. It has been found that such top surface recess may improve the spotting robustness of the SAF structure and ensure that the spotted nucleic acid probe is located as centrally of the SAF structure as desired. The risk of losing signal may thus be reduced.

The top surface recess is advantageously round. However, it may have other shapes such as oval or angular.

Advantageously the top surface recess has a center axis, which is parallel with the center axis of the SAF structure. The recess center axis is advantageously at most offset about 0.2 mm, such as at most offset about 0.1 mm from the center axis of the SAF structure. Preferably, the center axis of the surface recess is coincident with the center axis of the SAF structure.

Advantageously the recess has a substantially flat recess floor. The recess may for example have a diameter d, which about 10% of the top diameter D or more, such as from about 15% to about 80%, such as from about 20% to about 50 of the top diameter D. A recess diameter d from about 0.01 to about 0.2, such as from about 0.25 to about 0.1 is generally desired.

Advantageously the edge surrounding the recess at the top surface has a width of at least 0.01 mm. In practice, it may be expensive to produce the SAF structure with a top surface recess and a surrounding edge with a width below 0.005. On the other hand a very large edge width, such as 0.1 or larger or even 0.2 or larger, may result in a very small recess diameter d, which for some applications may be undesired.

It has been found that the recess advantageously should not be too high since this may reduce the read out signal. It is desired that the recess height h1 preferably should be less than 25% of the SAF height h, such as less than 20% of the SAF height h.

In an embodiment, the recess height h1 is about 0.05 mm or less, such as about 0.02 or less.

The edge of the recess may be sharp or rounded. In an embodiment the recess has rounded recess edge, preferably the recess edge is rounded with a with a rounding radius R, which is about 0.1 mm or less, such as between 0.01 and 0.8 mm.

In a preferred embodiment, the recess has a conical, frustum shape with a top surface formed by the surface formed by the floor. Hence, the recess conical, frustum shape is turned upside down relative to the SAF conical, frustum shape.

Preferably, the recess conical, frustum shape has a recess frustum angle θ, which is from about 40° to about 70°, such as from about 55° to about 65°, such as about 60°. It has been found that the signal may be increased where the recess frustum angle θ is close to the frustum angle α, such as up to 5 degrees in difference, preferably up to 2 degrees in difference. Preferably, the recess frustum angle θ is substantially identical to the frustum angle α.

Preferably, the test device is or form part of a cartridge comprising a channel with a channel surface defining the channel, wherein the solid substrate comprising the at least one SAF structure forms at least a part of the channel surface.

The cartridge may advantageously be as the microfluidic cartridge described in WO 2017/133741, with the difference that the SAF structure(s) is/are as described herein.

BRIEF DESCRIPTION OF THE DRAWINGS

The above and/or additional objects, features and advantages of the present invention will be further elucidated by the following illustrative and non-limiting description of embodiments and examples of the present invention, with reference to the appended drawings.

FIG. 10b is a plot of the average signal minus background of the images of FIG. 10a.

FIGS. 13a-13e are images of a number of immobilized polytails and nucleic acid probes obtained at different UV exposure time before and after wash wherein the UV emitter used was an 8 W UV emitter.

FIG. 15b are images of the immobilized nucleic acid probes of FIG. 15a.

FIG. 16b are images of the immobilized nucleic acid probes of FIG. 16a.

The figures are schematic and simplified for clarity. Throughout, the same reference numerals are used for identical or corresponding parts.

Figure 1:
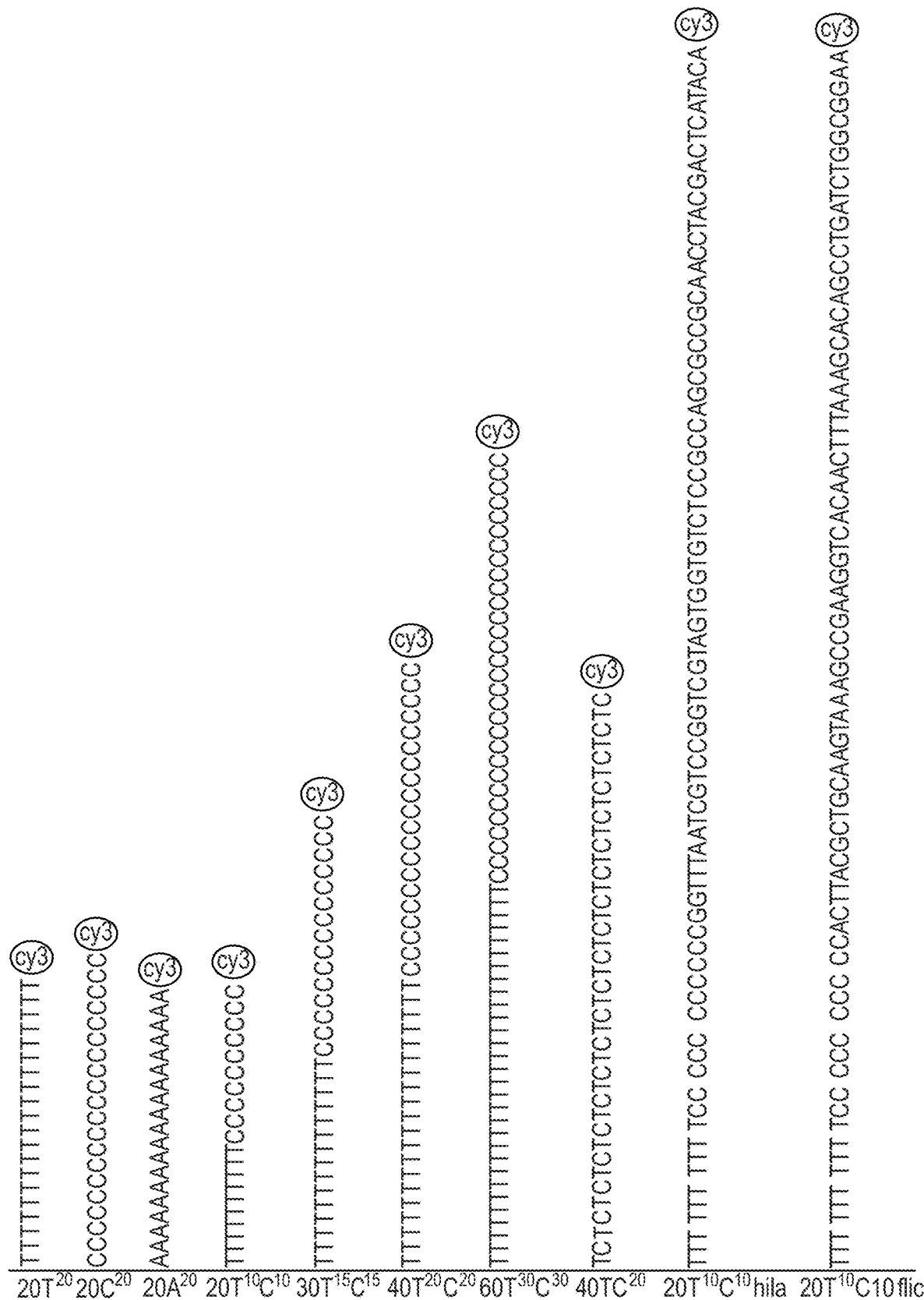
FIG. 1 is diagram showing a number of marked polytails tested in a first example a schematic top view of a microfluidic cartridge according to an embodiment of the invention.

Further scope of applicability of the present invention will become apparent from the description given hereinafter. However, it should be understood that the description and specific examples, while indicating preferred embodiments of the invention, are given by way of illustration only, since various changes and modifications within the spirit and scope of the invention will become apparent to those skilled in the art from this description and examples.

A simple UV cross-linking process scheme for attaching TC-tagged DNA oligonucleotides on various substrates was used. The process scheme used corresponds to the process scheme described in Sun Y, Perch-Nielsen I, Dufva M, et al. "Direct immobilization of DNA probes on non-modified plastics by UV irradiation and integration in microfluidic devices for rapid bioassay". Anal Bioanal Chem. 2012; 402(2):741-748. doi:10.1007/s00216-011-5459-4.

The technique has been showed to have not only high versatility but also high thermal stability comparable to other. In this study, this method was used to immobilize different marked polytails and marked nucleic acid probes to a PS solid support. The markers used in the below examples were fluorescence dyes. "Quasar 570" and "Cy3" were used as fluorescence dyes.

A number of different marked polytails and nucleic acid probes were used in the experiments including the following listed in table 1.

TABLE 1

Different polytail labelled with fluorescence dye for washing and thermocycling experiments.

| # | Polytail optional capture portion | and 5'-3' |
|---|---|---|
| 1 | $20T^{10}C^{10}$ (SEQ ID NO: 1) | TTTTTTTTTTCCCCCCCCCC/3'cy3 |
| 2 | $30T^{15}C^{15}$ (SEQ ID NO: 2) | TTTTTTTTTTTTTTTCCCCCCCCCCCCCCC/3'cy3 |
| 3 | $40T^{20}C^{20}$ (SEQ ID NO: 3) | TTTTTTTTTTTTTTTTTTTTCCCCCCCCCCCCCCCCCCCC/3'cy3 |
| 4 | $60T^{30}C^{30}$ (SEQ ID ON: 4) | TTTTTTTTTTTTTTTTTTTTTTTTTTTTTTCCCCCCCCCCCCCCCCCCCCCCCCCCCCCC/3'cy3 |
| 5 | $40TC^{20}$ (SEQ ID NO: 5) | TCTCTCTCTCTCTCTCTCTCTCTCTCTCTCTCTCTCTCTC/3'cy3 |
| 6 | $20T^{20}$ (SEQ ID NO: 6) | TTTTTTTTTTTTTTTTTTTT/3'cy3 |
| 7 | $20T^{10}C^{10}hilA$ (SEQ ID NO: 7) | TTTTTTTTTTCCCCCCCCCCGGTTTAATCGTCCGGTCGTAGTGGTGTCTCCGCCAGCGCCGCAACCTACGACTCATACA/3'cy3 |
| 8 | $20T^{10}C^{10}fliC$ (SEQ ID NO: 8) | TTTTTTTTTTCCCCCCCCCCACTTACGCTGCAAGTAAAGCCGAAGGTCACAACTTTAAAGCACAGCCTGATCTGGCGGAA/3'cy3 |
| 9 | $20C^{20}$ (SEQ ID NO: 9) | CCCCCCCCCCCCCCCCCCCC/3'cy3 |
| 10 | $20A^{20}$ (SEQ ID NO: 10) | AAAAAAAAAAAAAAAAAAAA-3'-Cy3 |
| 11 | $20G^{20}$ (SEQ ID NO: 11) | GGGGGGGGGGGGGGGGGGGG-3'-Cy3 |
| 12 | $40CT^{20}$ (SEQ ID NO: 12) | CTCTCTCTCTCTCTCTCTCTCTCTCTCTCTCTCTCTCTCT-quasar 570 |
| 13 | $40TTCC^{20}$ (SEQ ID NO: 13) | TTCCTTCCTTCCTTCCTTCCTTCCTTCCTTCCTTCCTTCC-quasar 570 |
| 14 | $42TTTCCC^{7}$ (SEQ ID NO: 14) | TTTCCCTTTCCCTTTCCCTTTCCCTTTCCCTTTCCCTTTCCC-quasar 570 |
| 15 | $40TTTTCCCC^{5}$ (SEQ ID NO: 15) | TTTTCCCCTTTTCCCCTTTTCCCCTTTTCCCCTTTTCCCC-quasar 570 |
| 16 | $42TTC^{14}$ (SEQ ID NO: 16) | TTCTTCTTCTTCTTCTTCTTCTTCTTCTTCTTCTTCTTCTTC-quasar 570 |
| 17 | $40TTTC^{10}$ (SEQ ID NO: 17) | TTTCTTTCTTTCTTTCTTTCTTTCTTTCTTTCTTTCTTTC-quasar 570 |
| 18 | $40TTTTC^{8}$ (SEQ ID NO: 18) | TTTTCTTTTCTTTTCTTTTCTTTTCTTTTCTTTTCTTTTC-quasar 570 |
| 19 | $39TCC^{13}$ (SEQ ID NO: 19) | TCCTCCTCCTCCTCCTCCTCCTCCTCCTCCTCCTCCTCC-quasar 570 |
| 20 | $40TCCC^{10}$ (SEQ ID NO: 20) | TCCCTCCCTCCCTCCCTCCCTCCCTCCCTCCCTCCCTCCC-quasar 570 |
| 21 | $39CT^{13}$ (SEQ ID NO: 21) | TCTTCTTCTTCTTCTTCTTCTTCTTCTTCTTCTTCTTCT-quasar 570 |
| 22 | $42TTCCTT^{7}$ (SEQ ID NO: 22) | TTCCTTTTCCTTTTCCTTTTCCTTTTCCTTTTCCTTTTCCTT-quasar 570 |

TABLE 1-continued

Different polytail labelled with fluorescence
dye for washing and thermocycling experiments.

| # | Polytail optional capture portion | and 5'-3' |
|---|---|---|
| 23 | 40TA[20] (SEQ ID NO: 23) | TATATATATATATATATATATATATATATATATATATATA-quasar 570 |
| 24 | 40TG[20] (SEQ ID NO: 24) | TGTGTGTGTGTGTGTGTGTGTGTGTGTGTGTGTGTGTGTG-quasar 570 |
| 25 | 40AG[20] (SEQ ID NO: 25) | AGAGAGAGAGAGAGAGAGAGAGAGAGAGAGAGAGAGAGAG-quasar 570 |
| 26 | 40GC[20] (SEQ ID NO: 26) | GCGCGCGCGCGCGCGCGCGCGCGCGCGCGCGCGCGCGCGC-quasar 570 |
| 27 | 40AC[20] (SEQ ID NO: 27) | ACACACACACACACACACACACACACACACACACACACAC-quasar 570 |
| 28 | 39CG[13] (SEQ ID NO: 28) | TCGTCGTCGTCGTCGTCGTCGTCGTCGTCGTCGTCGTCG-quasar 570 |
| 29 | 40TTCG[10] (SEQ ID NO: 29) | TTCGTTCGTTCGTTCGTTCGTTCGTTCGTTCGTTCGTTCG-quasar 570 |
| 30 | 40TAGC[10] (SEQ ID NO: 30) | TAGCTAGCTAGCTAGCTAGCTAGCTAGCTAGCTAGCTAGC-quasar 570 |

The nucleic acid probes or nucleic acid probes comprising polytails of numbers 5, 12, 13, 14, 15, 16, 17, 18, 19, 20, 21, 22 and 29 are examples of the inventions. The remaining nucleic acid probes or nucleic acid probes comprising polytails are comparative examples.

EXAMPLE 1

In this example, the nucleic acid probes or nucleic acid probes comprising polytails of numbers 6, 9, 10, 1, 2, 3, 4, 5, 7, 8 (in the order as shown in FIG. 1).

The polytails/nucleic acid probes were diluted in 5× saline sodium citrate (SSC) buffer (Promega, WI, USA) with 0.04% Triton X-100 (Sigma-Aldrich, USA). The polytails/nucleic acid probes solutions were spotted onto a cleaned PS slides using a non-contact sciFLEXARRAYER S11 spotting machine (Scienion, Germany). Each polytails/nucleic acid probes solution was spotted in four consecutive spots. After drying, the slides were exposed to UV irradiation at 254 nm with energy of 1.8 Joule/cm$^2$ in an Ultraviolet Crosslinkers (UVP, Fisher Scientific, Denmark) to immobilize the polytails/nucleic acid probes onto surface of the substrate.

Thereafter the solid support (PS slide) was washed for 5 minutes using milliQ water obtained from Millipore Corporation. The MilliQ water was 'ultrapure' water of "Type 1", as defined by various authorities (e.g. ISO 3696), After the UV exposure the immobilization efficiency (immobilization percent) was measured and determined as follows The immobilization efficiency was calculated as below equation:

$$\frac{\text{Signal obtained after washing}}{\text{Signal obtained after } UV \text{ crosslink}} \times 100\% =$$

Immobilization efficiency of washing.

Figure 2:
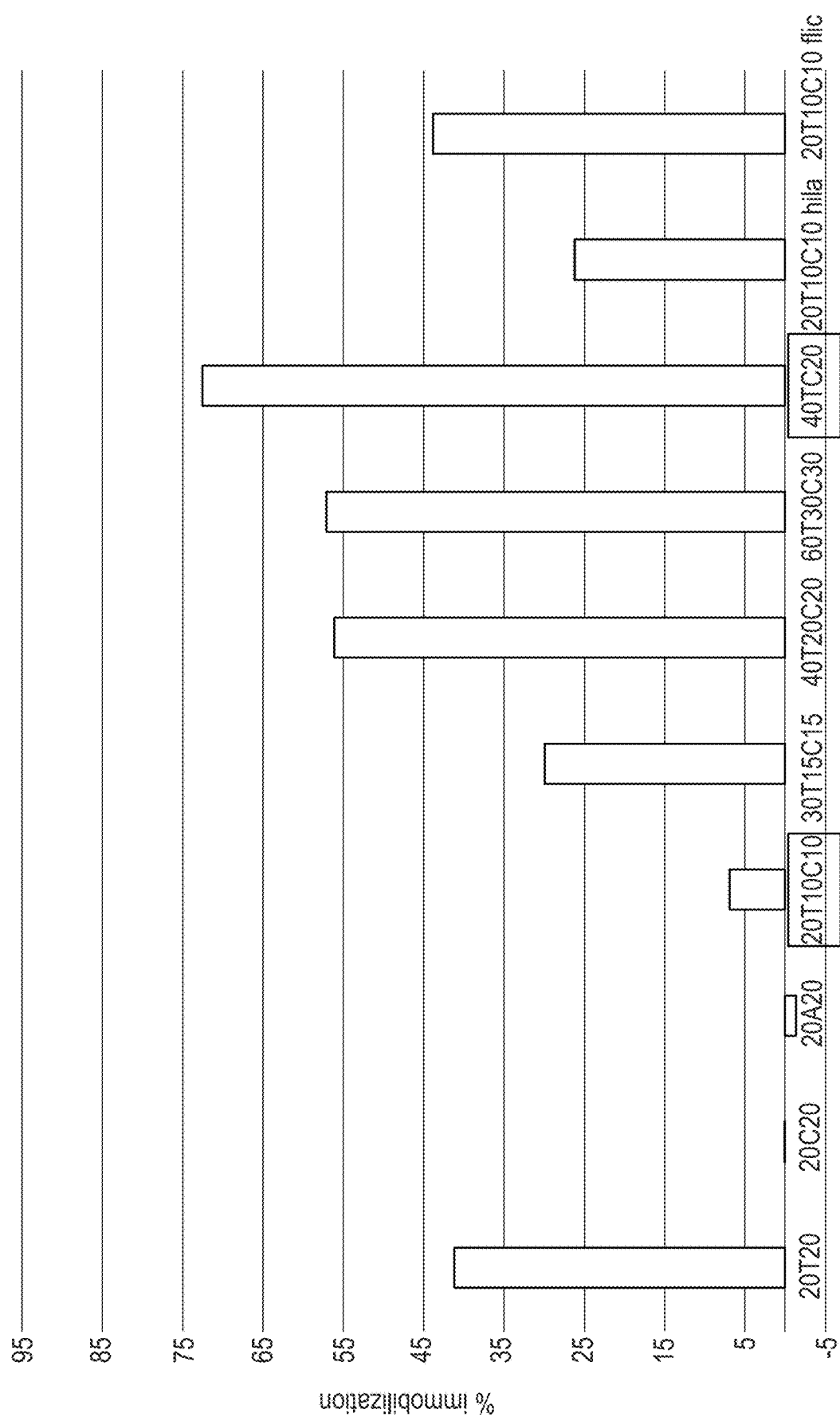
FIG. 2 is diagram showing the immobilization percent's of the respective marked polytails in the first example.

The results are shown in FIG. 2. It can be seen that the polytail 40TC[20] (SEQ ID NO:5) (the number 5 polytail as listed above) has a much higher immobilization efficiency than the comparative polytails.

EXAMPLE 2

Figure 3:
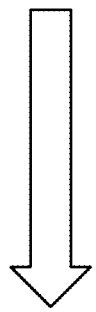
FIG. 3 is a process diagram applied in a further example.
Figure 3:
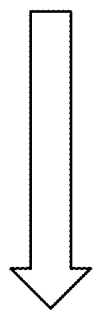

This example was conducted following the process diagram shown in FIG. 3.

Figure 4:
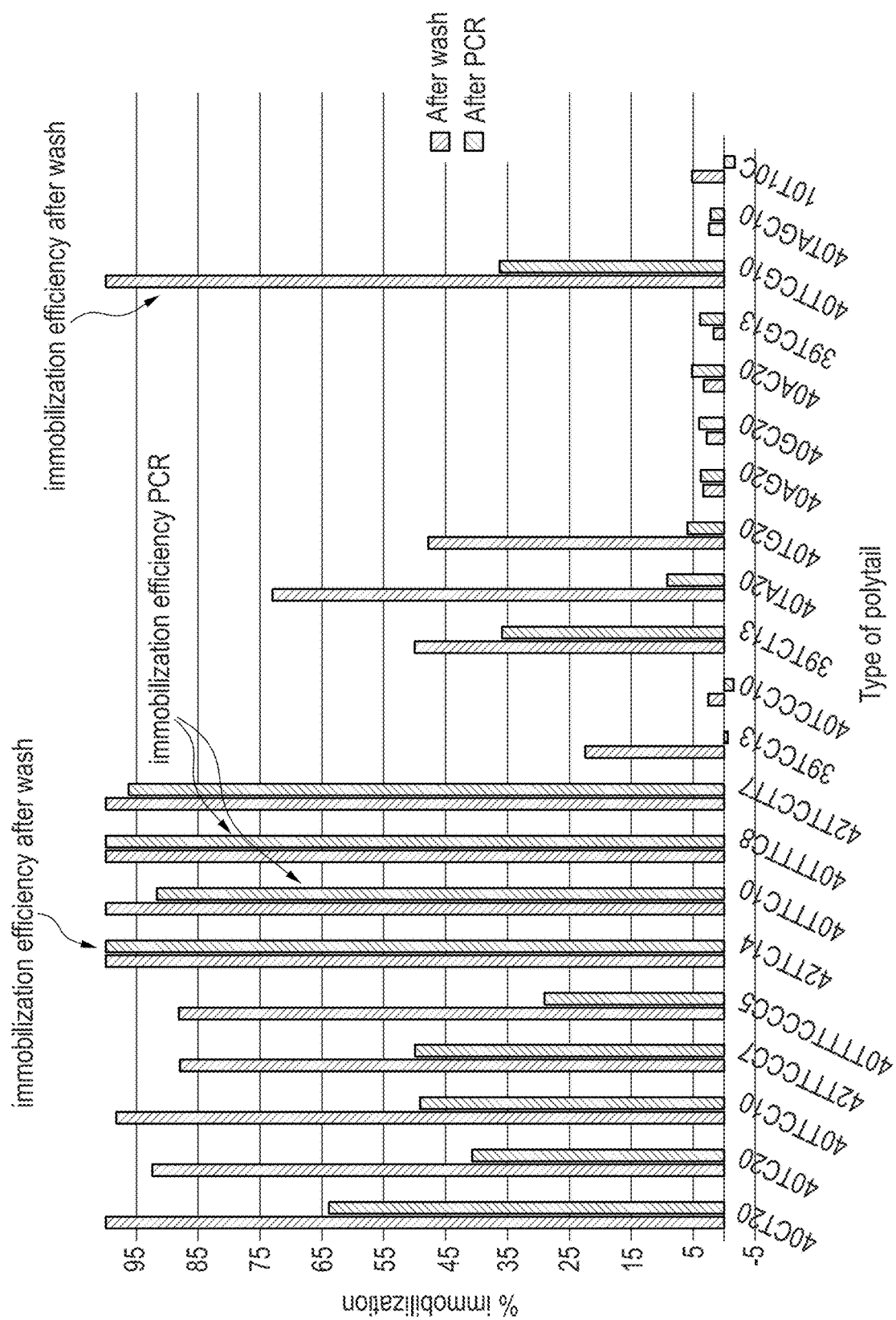
FIG. 4 is diagram showing the immobilization percent's of a number of marked polytails tested in the further example.

Different lengths and configurations of TC polytails/nucleic acid probes with different polytails were used. The marked polytails/nucleic acid probe used was as follows (mentioned in the order from left to right as shown in FIG. 4) Numbers 12, 5, 13, 14, 15, 16, 17, 18, 22, 19, 20, 21, 23, 24, 25, 26, 27, 28, 29, 30.

The polytails/nucleic acid probes were immobilized using the same procedure as described in example 1. Thereafter the solid support was washed.

The signals of different polytails/probes were obtained by microscope after spotted and UV crosslink. Next, the slides were washed with 0.1× saline sodium citrate (SSC) buffer for 5 minutes and another 5 minutes in MilliQ water to remove un-attached probe and fluorescence signal.

The solid support was imaged and the immobilization efficiency was calculated as below equation:

$$\frac{\text{Signal obtained after washing}}{\text{Signal obtained after } UV \text{ crosslink}} \times 100\% =$$

Immobilization efficiency of washing.

The immobilization efficiency after wash for each polytails/nucleic acid probe is shown as the first columns on FIG. 4.

EXAMPLE 3

The immobilized and washed polytails/nucleic acid probes were thereafter subjected to treatment conditions corresponding to harsh SP-PCR thermocycler treatment conditions.

The immobilized polytails/probes were subjected different temperature by the PCR program of 94° C. for 2 minutes follow by 30 cycles of 94° C. for 10 seconds, 60° C. for 20 seconds, 72° C. for 20 seconds, then another 15 PCR cycles of 94° C. for 10 seconds, 65° C. for 20 seconds, 72° C. for 20 seconds. The polytail were tested in a flat-bed PCR thermocycler (Proflex, Thermo fisher) and fluorescence signal were obtained.

The immobilized efficiency after PCR thermocycler treatment was calculated as follows:

$$\frac{\text{Signal obtained after thermo cycler}}{\text{Signal obtained after } UV \text{ crosslink}} \times 100\% = \quad (2)$$

Immobilization efficiency of thermo cycler.

The immobilization efficiency after PCR thermocycler treatment for each polytails/nucleic acid probe is shown as the second columns on FIG. 4.

It can be seen that the immobilization efficiency both after washing and in particular after the PCR thermocycler treatment is much higher for the nucleic acid probes of the present invention. In particular, the above mentioned preferred nucleic acid probes show an extraordinary high immobilization efficiency.

Figure 5:
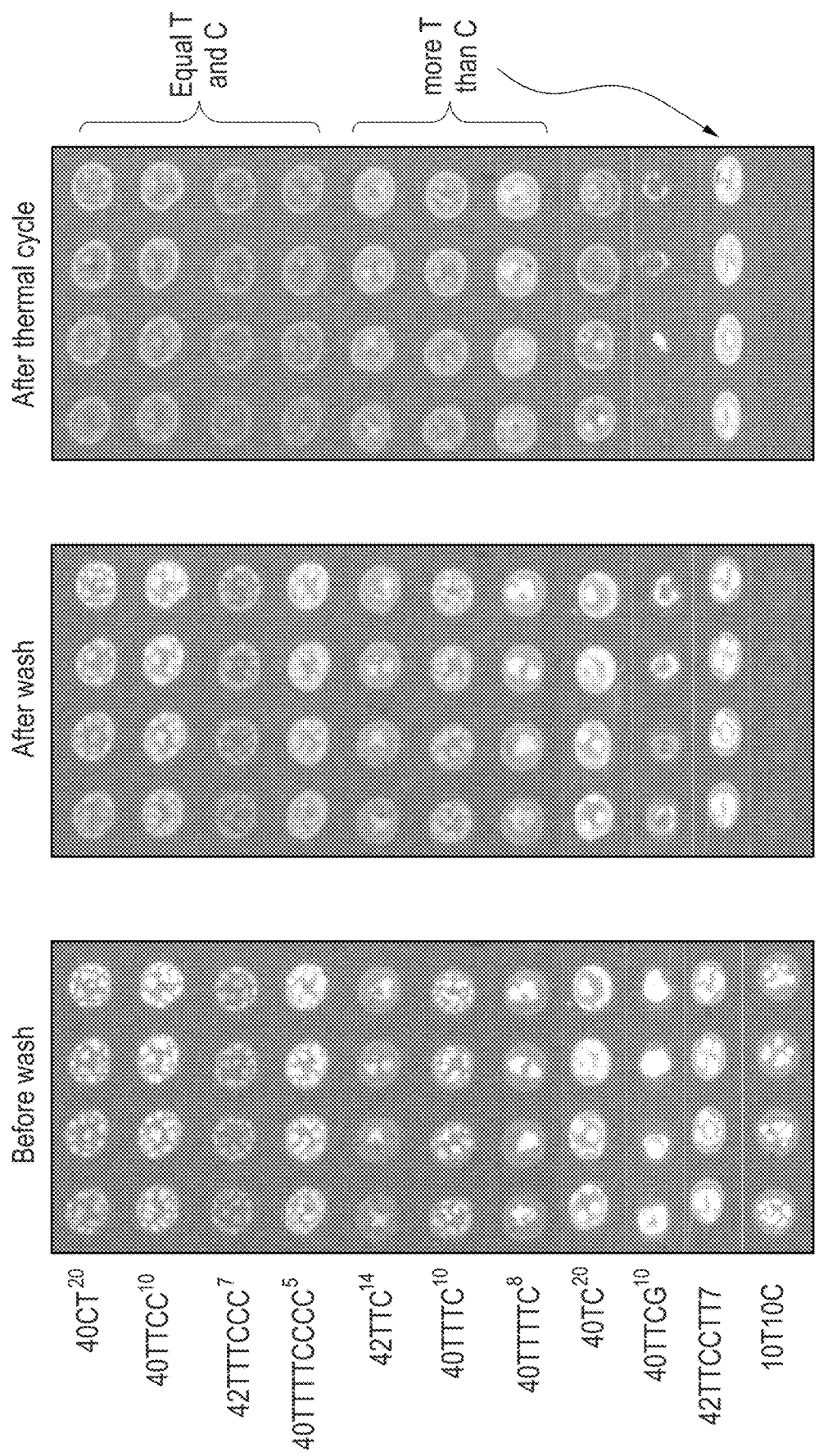
FIG. 5 are images of the spots of the polytails in the further example.

The images acquired of the PS slides solid support in examples 2 and 3 are shown in FIG. 5. Clearly, the nucleic acid probes with polytails having more base type T have an exceptional high immobilization efficiency.

EXAMPLE 4

Figure 6:
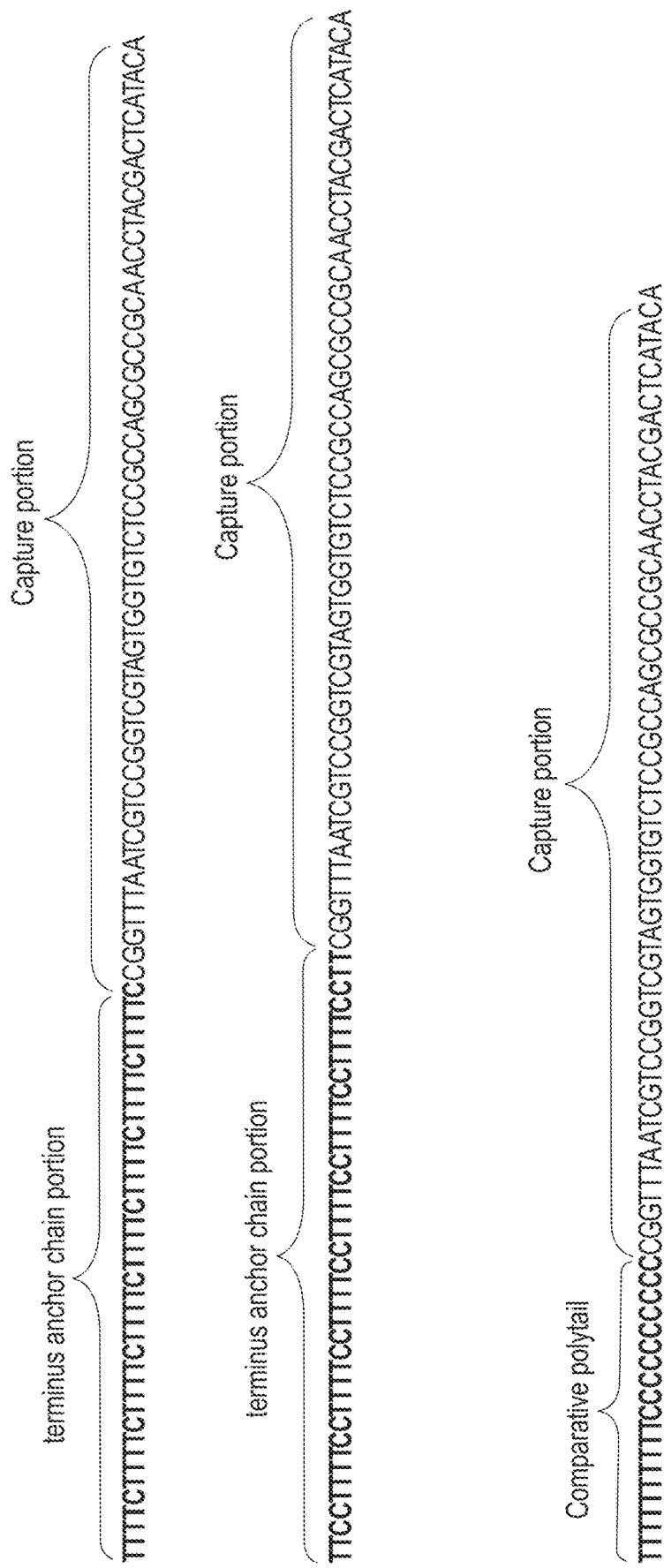
FIG. 6 shows two nucleic acid probes of embodiments of the invention and one nucleic acid probe having a comparative polytail (terminus anchor chain portion)

3 different nucleic acid probes were synthesized comprising a) a first nucleic acid probe according to an embodiment of the invention had a polytail of the nucleotide sequence 40TTTC$^8$ (SEQ ID NO:18) and a capture portion targeting a hilA gene, b) a second nucleic acid probe according to an embodiment of the invention had a polytail of the nucleotide sequence 42TTCCTT$^7$ (SEQ ID NO:22) and a capture portion targeting the hilA gene and c) a comparative nucleic acid probe with a polytail of the nucleotide sequence 20T$^{10}$C$^{10}$ (SEQ ID NO:1) and a capture portion with hilA gene for detecting *Salmonella* spp. The nucleic acid probes are shown in FIG. 6.

The nucleic acid probes were spotted to a solid support (PS substrate) in different concentrations ranging from 1 μM to 60 μM.

A 25 μL of SP-PCR reaction mixture was prepared. The SP-PCR mixture consists of 1× Phusion® Human Specimen PCR Buffer (Thermo Fisher Scientific), 400 nM of hilA forward and 1600 nM hilA reverse primers, and 0.05 U/μL Phusion Hot Start II High-Fidelity DNA polymerase (Thermo Fisher Scientific). A Gene Frame (Thermo Fisher Scientific) was used to create a 25 μL reaction chamber surrounding the solid support primer array. The PCR master mix was loaded by pipette into the gene frame and sealed with a cover slip. The PS slide was spotted with the nucleic acid probes. The SP-PCR was conducted in a flat-bed PCR thermocycler, where a piece of 1 cm thick polystyrene insulation foam was used to separate the slides from the lid of the PCR thermocycler. The SP-PCR conditions were: 94° C. 2 minutes follow by 30 cycles of 94° C. for 10 seconds, 60° C. for 20 seconds, 72° C. for 20 seconds, then another 15 PCR cycles of 94° C. for 10 seconds, 65° C. for 20 seconds, 72° C. for 20 seconds. A higher annealing temperature was used in the later 15 PCR cycles to enhance the SP-PCR. After the SP-PCR, the chamber was washed with 0.1×SSC and 0.1% of Sodium dodecyl sulphate (SDS) (Promega, WI, USA) for 5 minutes then rinsed with deionized water and dried at room temperature. The slide was ready for scanning.

After the SP-PCR, the slides were scanned using a microscope (ZEISS Axiovert 200, Germany). Microarray image was analysed using ImageJ software (Molecular devices). A circle was drawn and adjusted to the size of the spot and the mean light intensity value was determined as signal. Another circle was drawn nearby was used as the background. The signal in this study was defined as the signal of the 4 spots on the array, subtracting the mean background.

Figure 7:
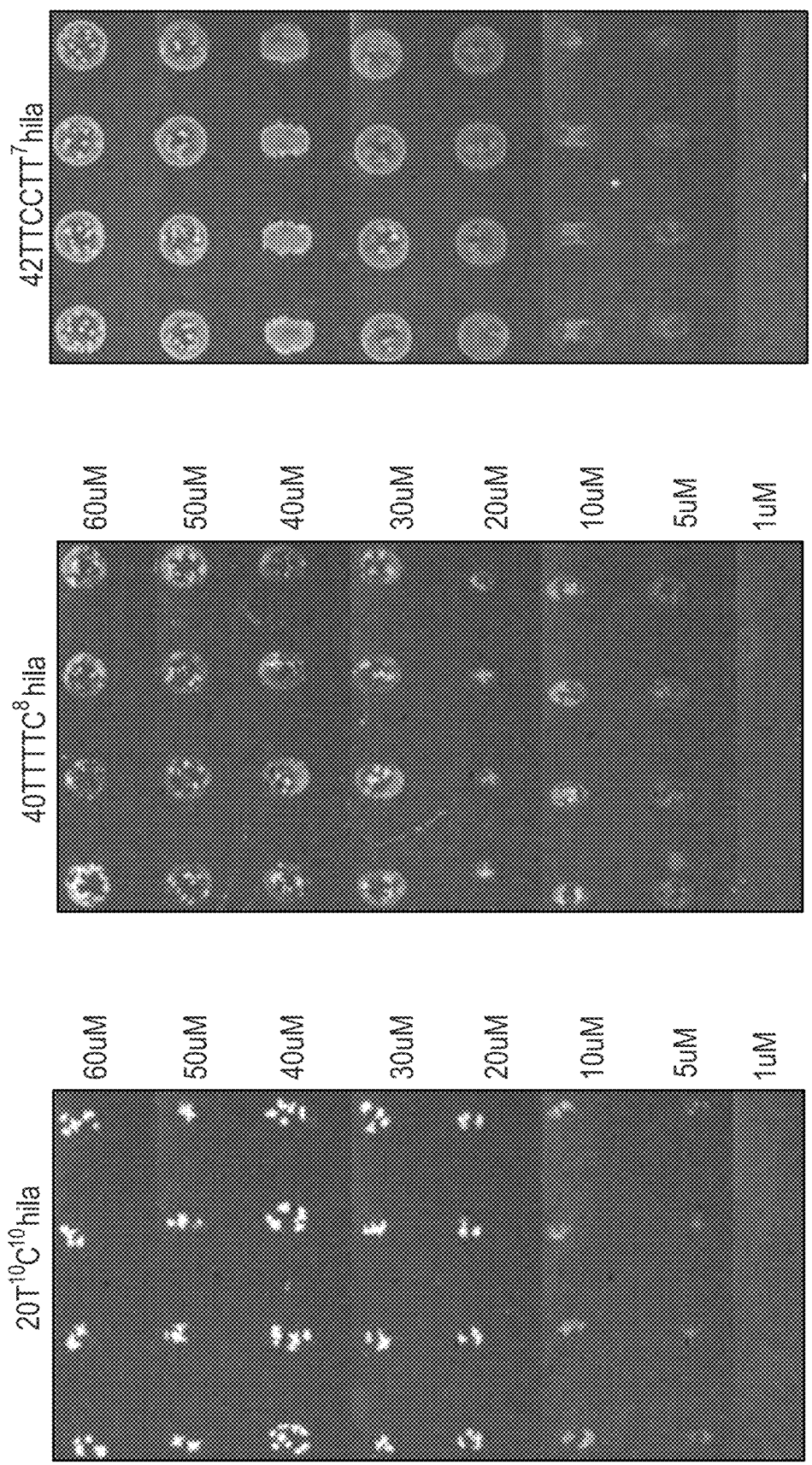
FIG. 7 shows images of different concentration of the nucleic acid probes of FIGS. 6a and 6b where the nucleic acid probes are marked.

FIG. 7 shows the resulting immobilization efficiency at different nucleic acid probe concentrations after the PS-PCR. It can easily be seen that the nucleic acid probes of the invention has a much higher immobilization efficiency than the comparative nucleic acid probe.

Figure 8:
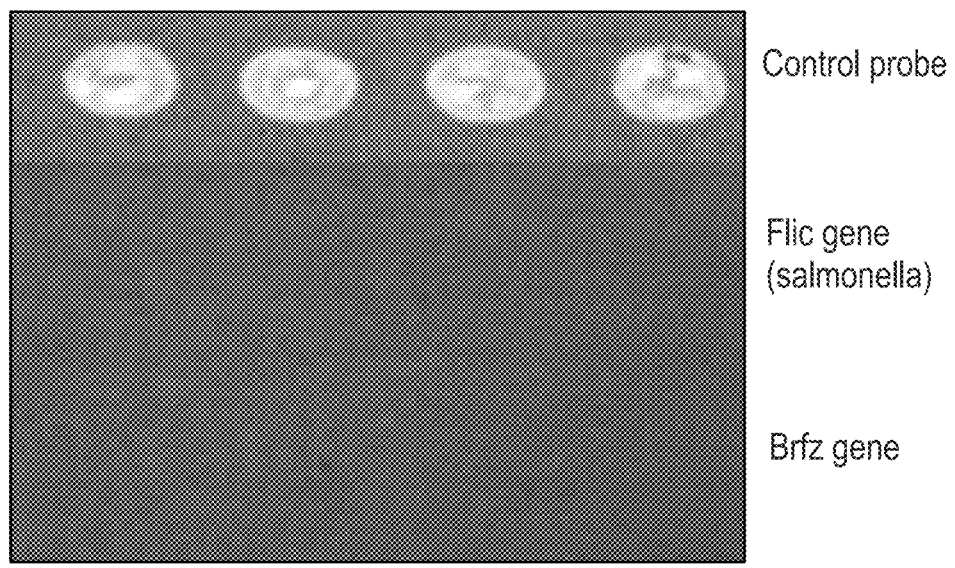
FIG. 8 is an image of a control probe and two different capture portions—a Flic gene that targeting *salmonella* and a Brfz gene that targeting *Bordetella* bacteria.

FIG. 8 is an image of a control probe and two different capture portions—a Flic gene that targeting *salmonella* and a Brtz gene that targeting *Bordetella* bacteria. As control probe the polytail 42TTCCTT$^7$ (SEQ ID NO:22) was used As shown in FIG. 7, the polytail 42TTCCTT$^7$ (SEQ ID NO:22) that targeting *Salmonella* spp. showed about the same round shape after SP PCR than before, which means that the 42TTCCTT$^7$ (SEQ ID NO:22) polytail help the entire probe to be immobilized on the surface with a very high bonding efficiency.

Figure 9A:
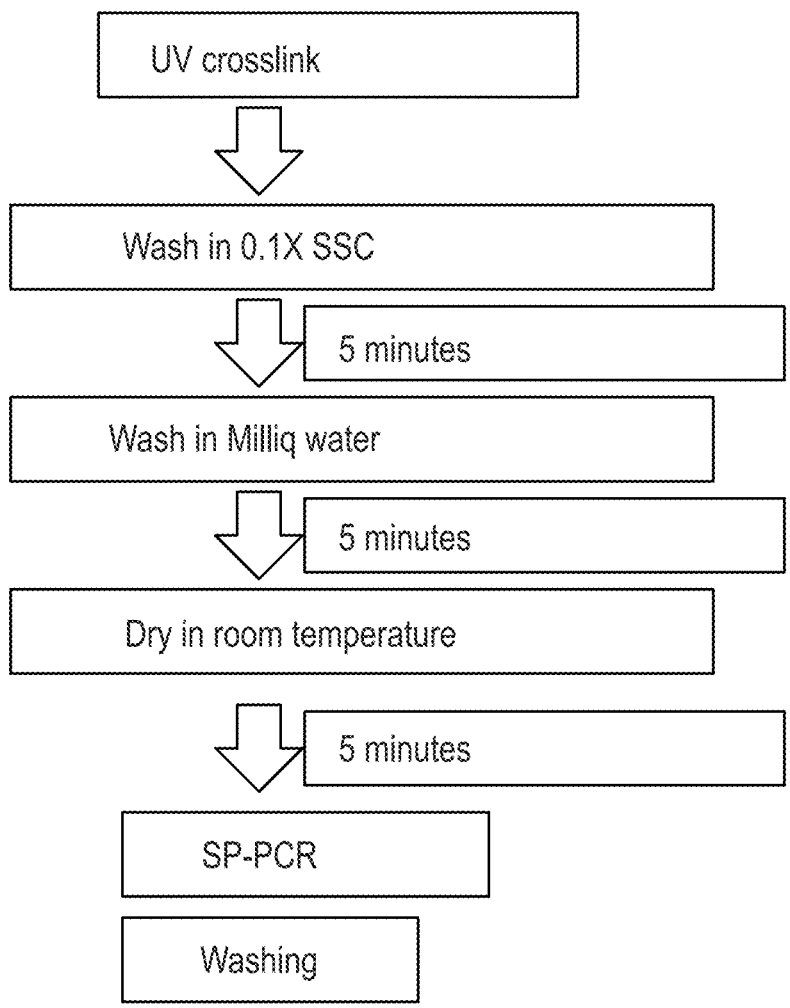
FIG. 9a show a first process scheme for performing SP-PCR.
Figure 9B:
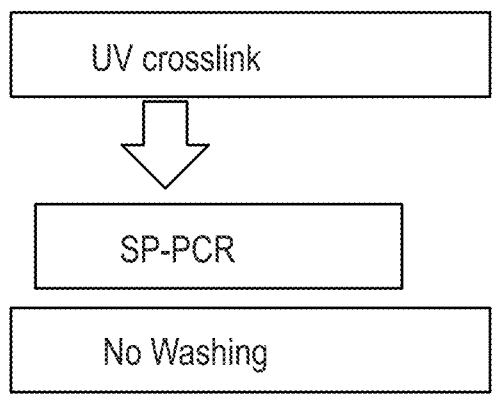
FIG. 9b show a second process scheme for performing SP-PCR.

The first process scheme for performing SP-PCR shown in FIG. 9*a* is a standard process scheme The second process scheme for performing SP-PCR shown in FIG. 9*b* is a novel SP-PCR process, which has been made available due to the present invention.

Thanks to the high immobilization efficiency provided by the nucleic acid probes and the method of the invention the SP-PCR may now be performed without washing after the UV crosslinking (immobilization) and/or without washing after the PS-PCR procedure.

Figure 10A:
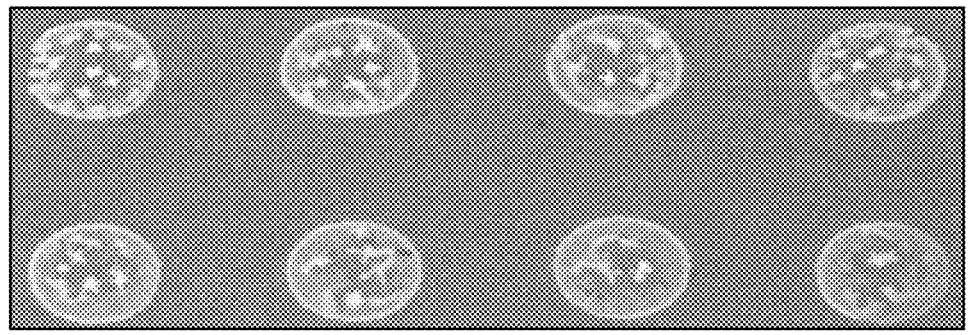
FIG. 10a are images of a solid support with spotted nucleic acid probes subject to SP-PCR with and without washing.
Figure 10A:
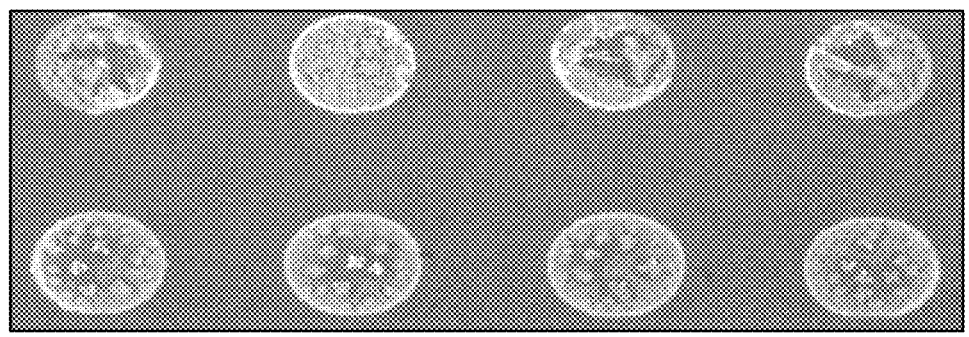

FIG. 10*a* are images of a solid support with spotted nucleic acid probes subject to SP-PCR with and without washing.

EXAMPLE 5

In example 5 the two nucleic acid probes of example 5 which represent embodiments of the invention namely the nucleic acid probe a) a first nucleic acid probe according to an embodiment of the invention had a polytail of the nucleotide sequence 40TTTC$^8$ (SEQ ID NO:18) and a capture portion targeting a hilA gene and b) a second nucleic acid probe according to an embodiment of the invention had a polytail of the nucleotide sequence 42TTCCTT$^7$ (SEQ ID NO:22) and a capture portion targeting the hilA gene were used.

The spotting and the SP-PCR procedure was performed following the procedure of example 4 using a nucleic acid probe concentration of 60 μM.

Figure 10B:
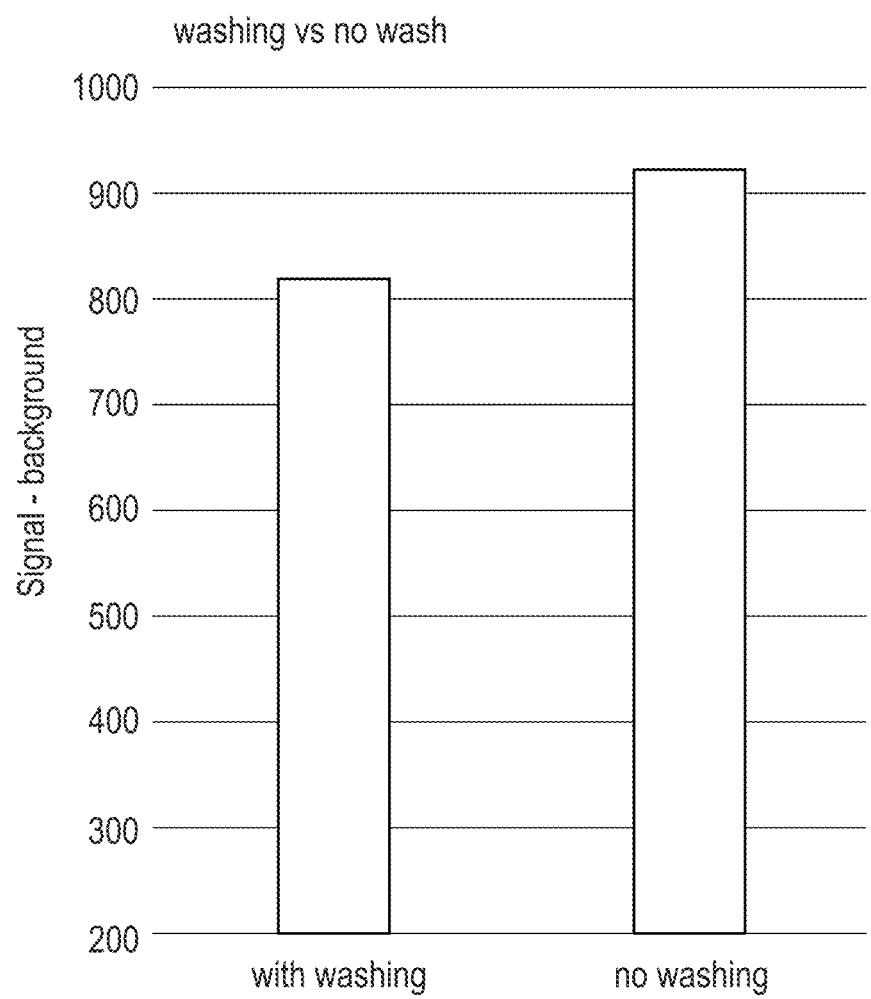

The result is shown in FIG. 10*a* prior to washing and after washing. FIG. 10*b* shows the average of the signal minus background with washing and without washing and it can be seen that there is a relatively low amount a false positive in the non-washed samples.

EXAMPLE 6

A number of different marked polytail/nucleic acid probes were subjected to different UV exposure time and different UV dose for immobilization. The polytail/nucleic acid probes used were as shown in FIG. 1.

The polytail/nucleic acid probes were spotted to the solid support as described in example 1 but with different UV exposure.

Four spots of each polytails/nucleic acid probe were subjected to an UV exposure from an 8 W UV emitter for 3 minutes. Four spots of each polytails/nucleic acid probe were subjected to an UV exposure from a 16 W UV emitter for 8 minutes.

Figure 11:
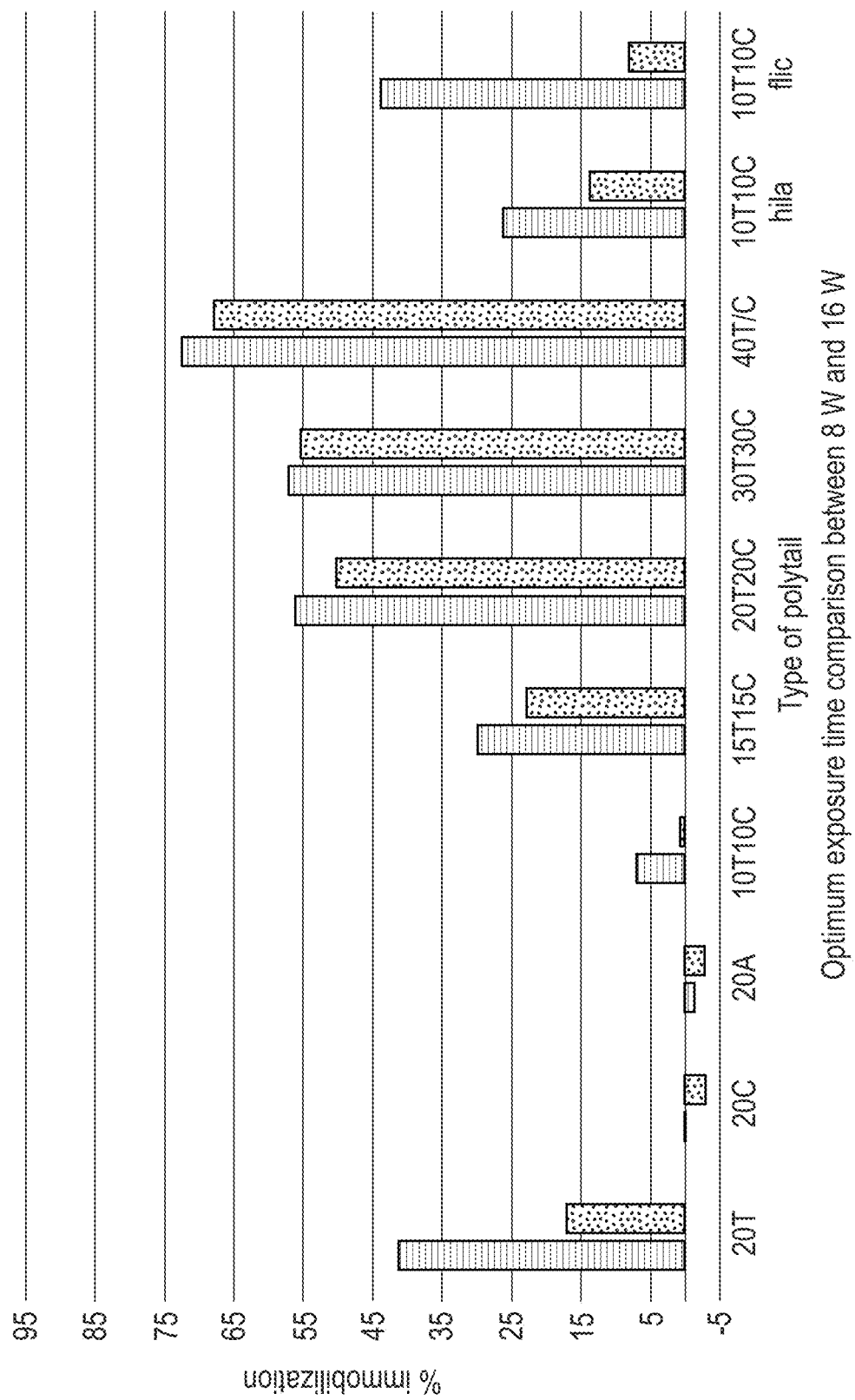
FIG. 11 is a diagram showing the immobilization percent's of a number of marked polytails and nucleic acid probes where the polytails/nucleic acid probes are immobilized using different UV exposure time.

The result is shown in FIG. 11 where the left plot for each polytail/nucleic acid probe is the 8 W UV emitter for 3 minutes treatment and the right left plot for each polytail/nucleic acid probe is the 16 W UV emitter for 8 minutes treatment. It appears that the 8 W UV emitter for 3 minutes treatment is better than the 16 W UV emitter for 8 minutes treatment.

EXAMPLE 7

A marked polytail with the sequence 40 T/C (also called 40TC$^{20}$) (SEQ ID NO:5) was used in this test. Samples of the polytail were spotted to the solid support as described in example 1 but with different UV exposure.

Figure 12:
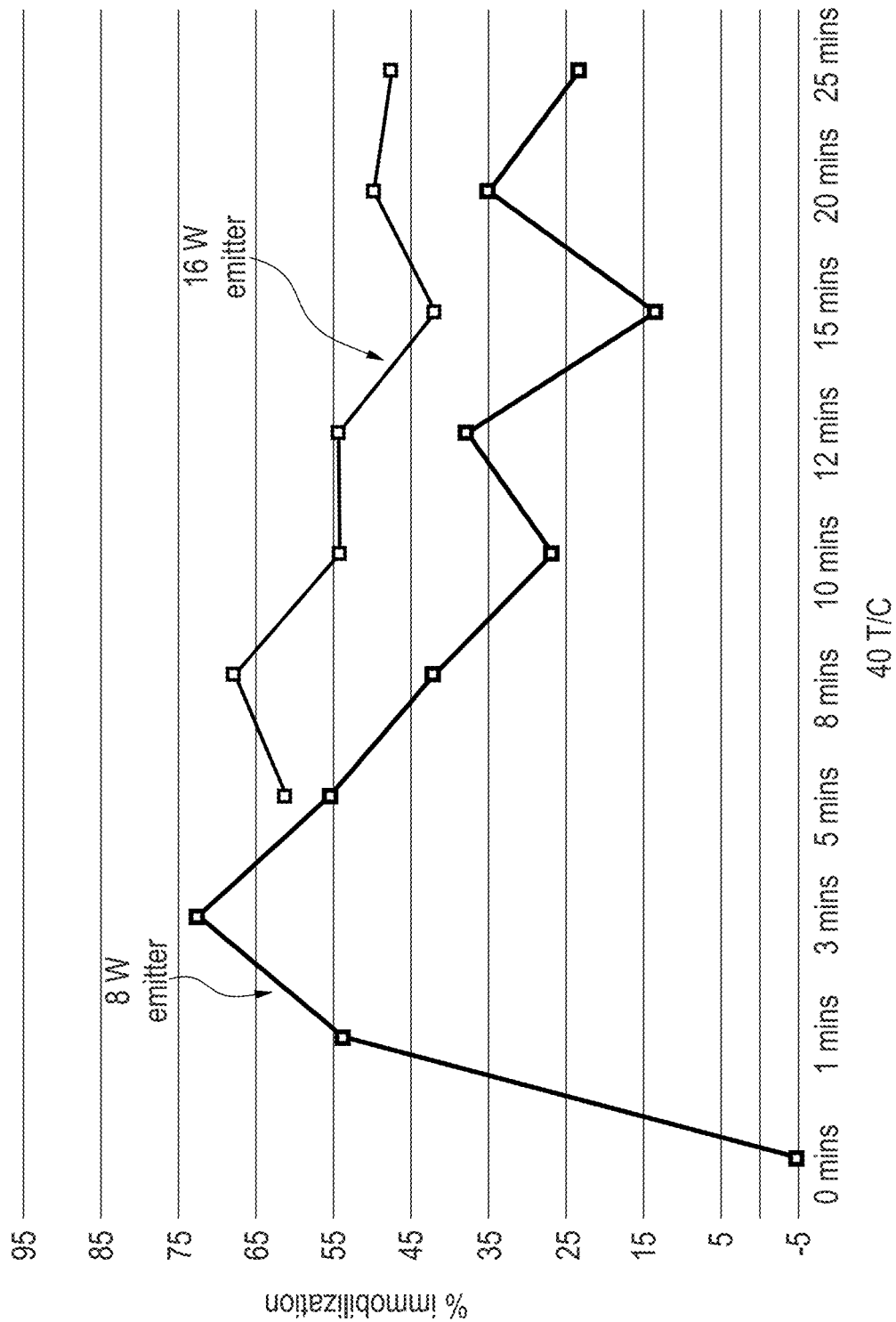
FIG. 12 show the immobilization percent as a function of UV exposure time for a marked polytail.
Figure 13A:
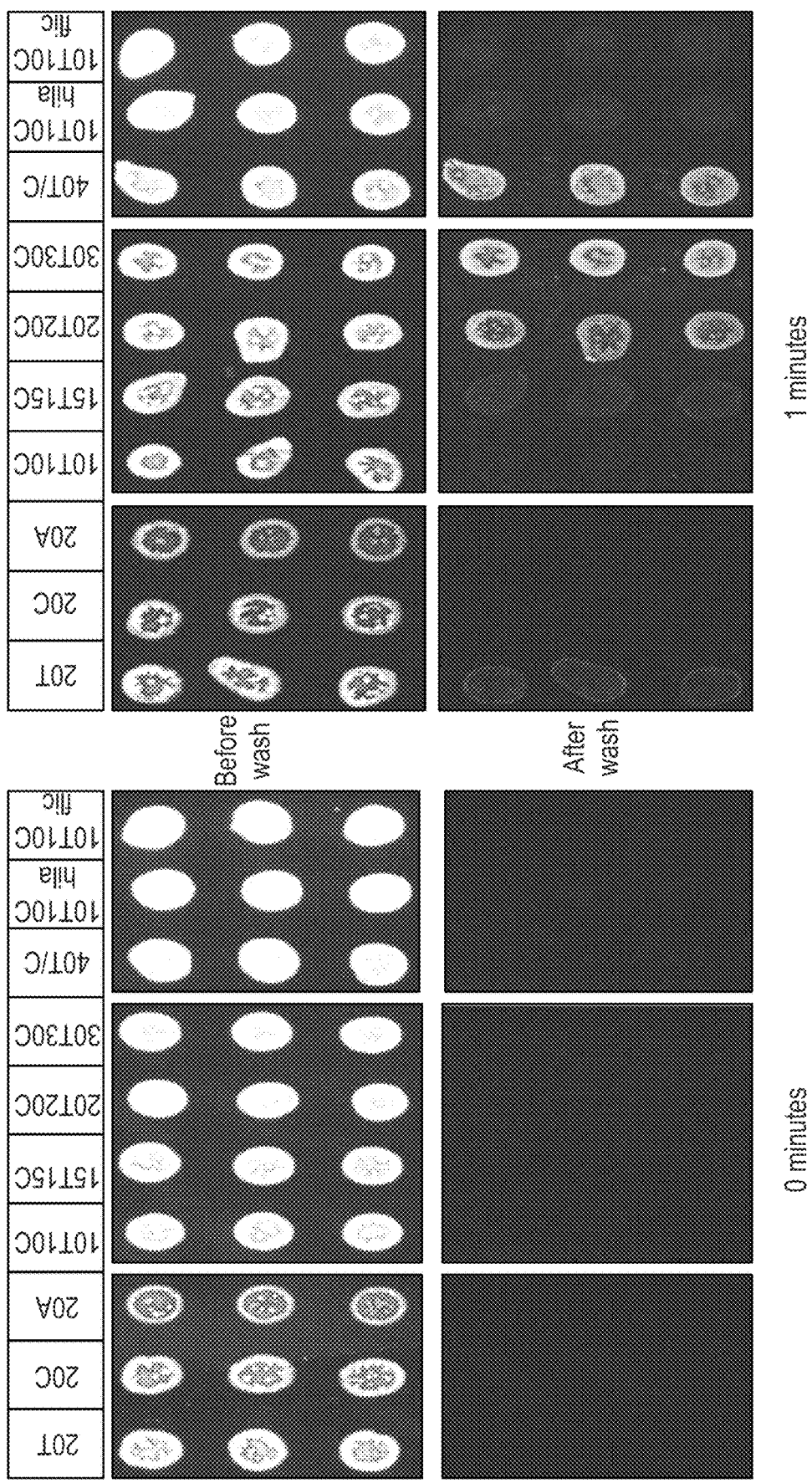
Figure 13B:
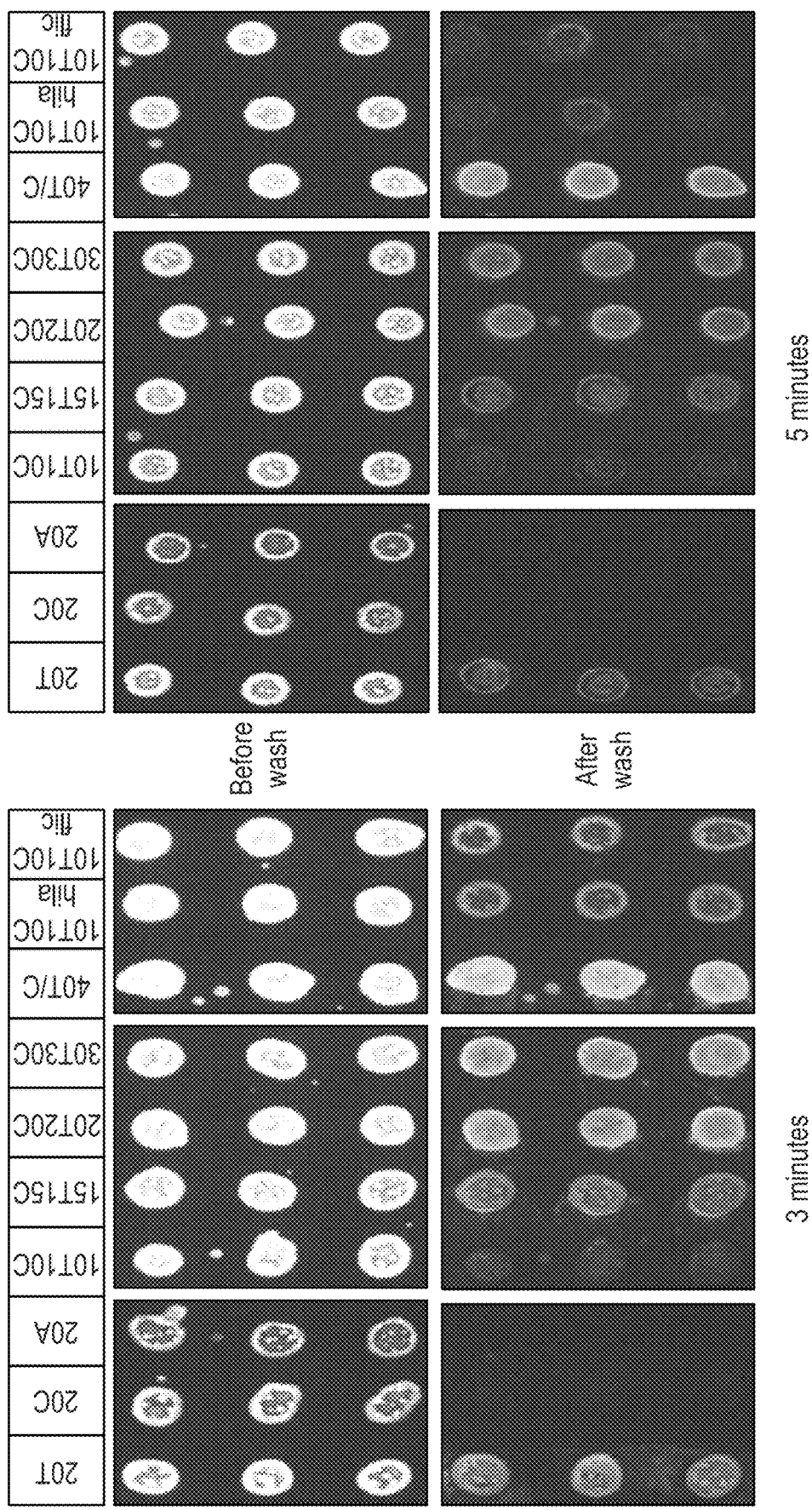
Figure 13C:
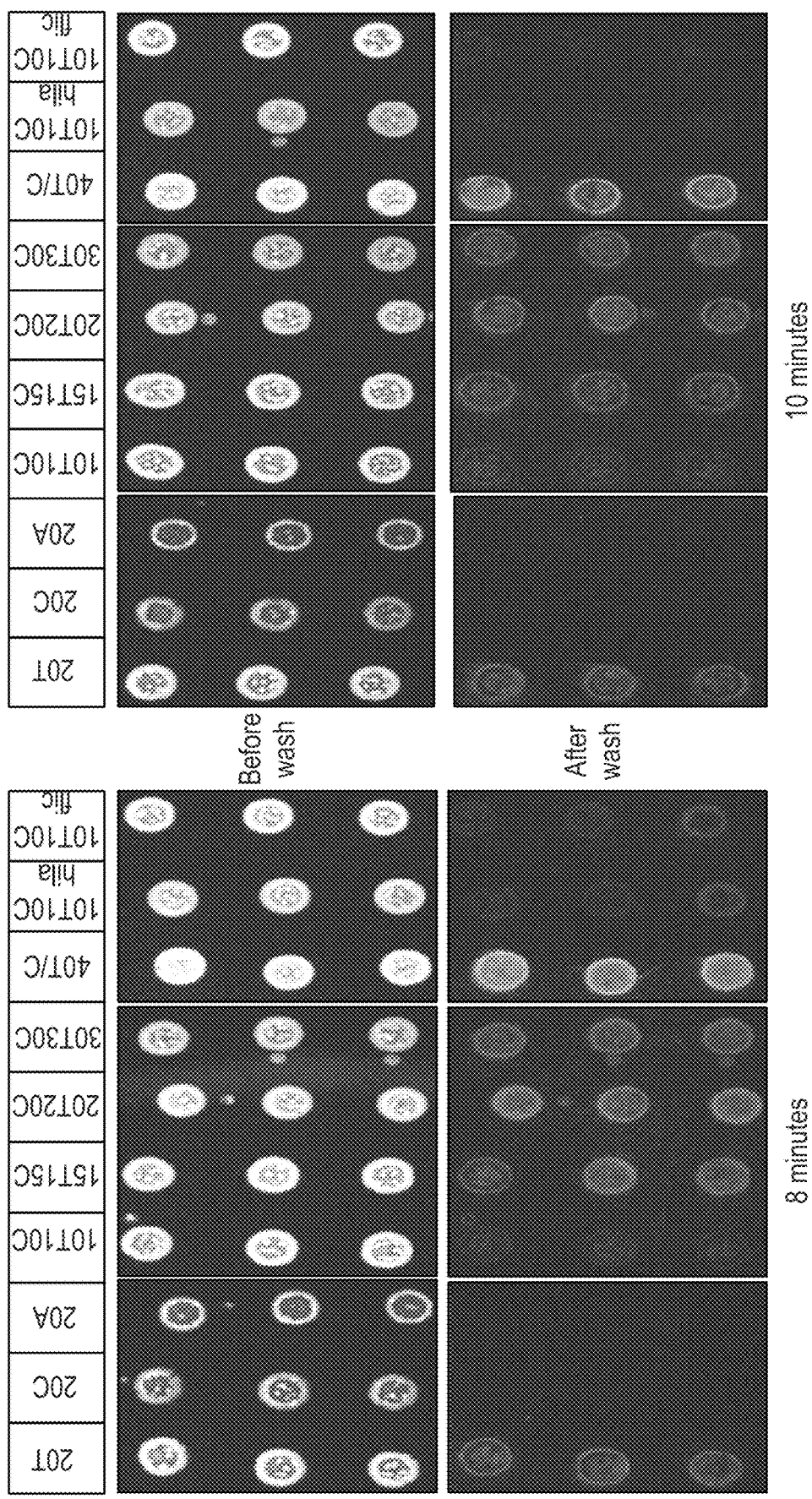
Figure 13D:
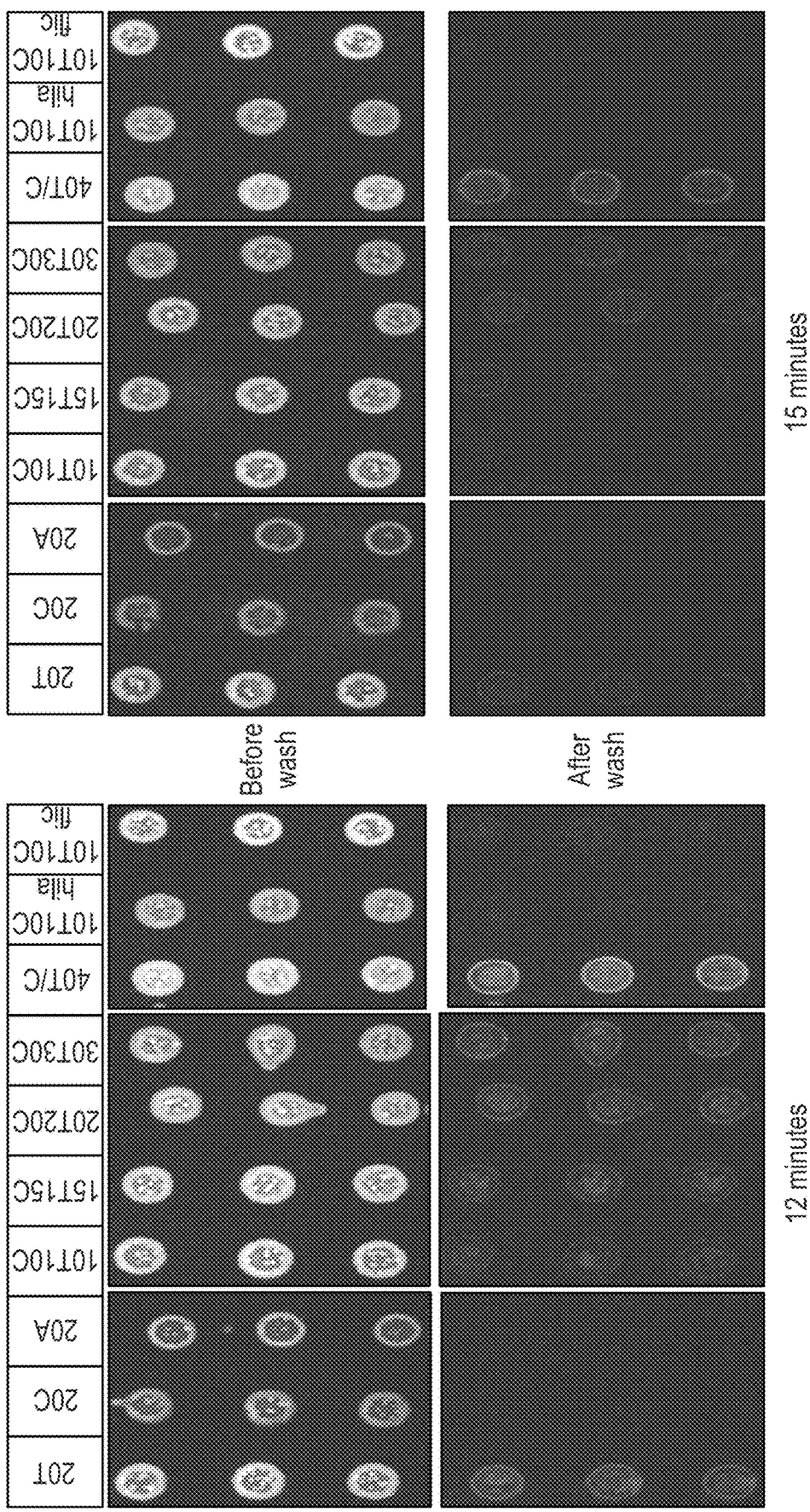

For some samples the 8 W UV emitter was used and for other the 16 W UV emitter was used. The exposure time was varied as shown in FIG. 12 where the immobilization efficiency after wash is plotted as a function of the exposure time for each of the two emitters.

It can be seen that the lower watt (8 Watt UV emitter) is better than the higher watt emitter. Further, the 8 W emitter has an immobilization optimum around 3 minutes which means that the nucleic acid probe can be immobilized a rather low UV dosage, which is highly advantageous since the risk of damaging the capture portion thereby may be reduced or even avoided.

In an embodiment of the invention the nucleic acid probe had a polytail of the nucleotide sequence 40TTTTC$^8$ (SEQ ID NO: 18) and a capture portion targeting a hilA gene was used.

3 different nucleic acid probes was synthesized and c) a comparative nucleic acid probe with a polytail of the nucleotide sequence 20T$^{10}$C$^{10}$ (SEQ ID NO:1) and a capture portion with hilA gene for detecting *Salmonella* spp. The nucleic acid probes are shown in FIG. 6.

In FIGS. 13a-13e the images of the immobilized polytails obtained at the different UV exposure time before and after wash using the 8 W UV emitter are shown.

Figure 14A:
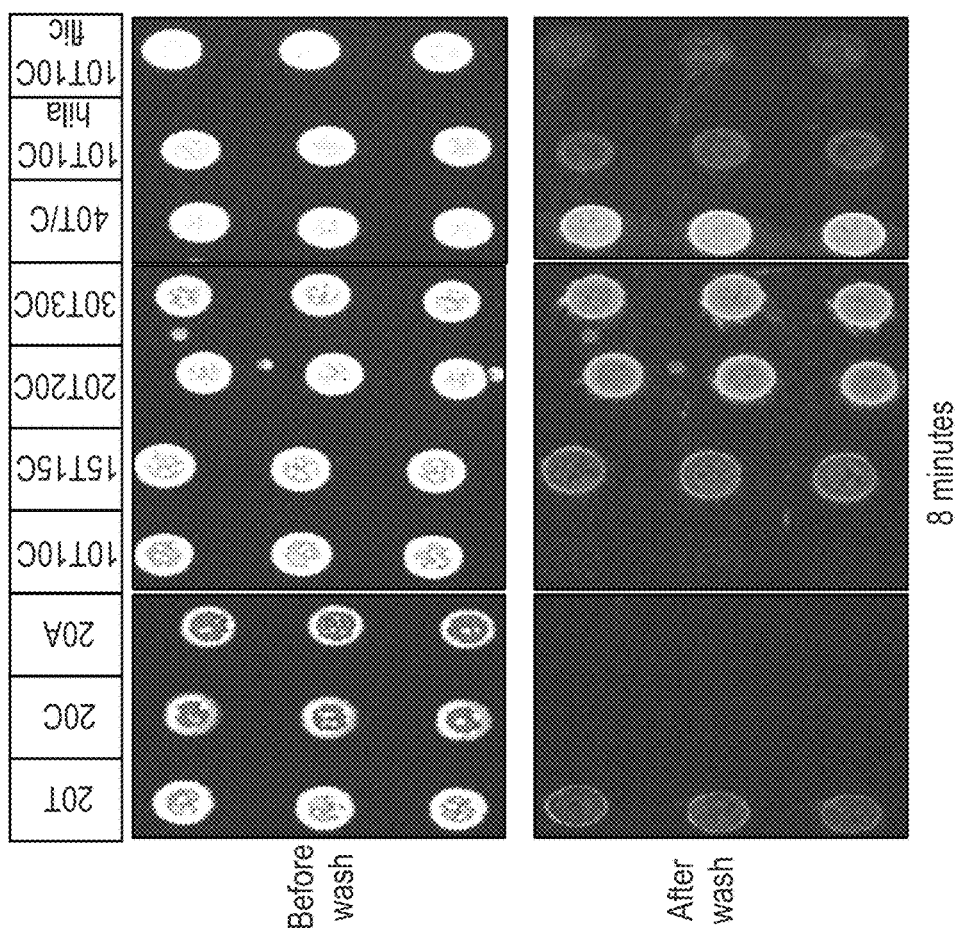
FIGS. 14a-14c are images of a number of immobilized polytails and nucleic acid probes obtained at different UV exposure time before and after wash wherein the UV emitter used was a 16 W UV emitter.
Figure 14A:
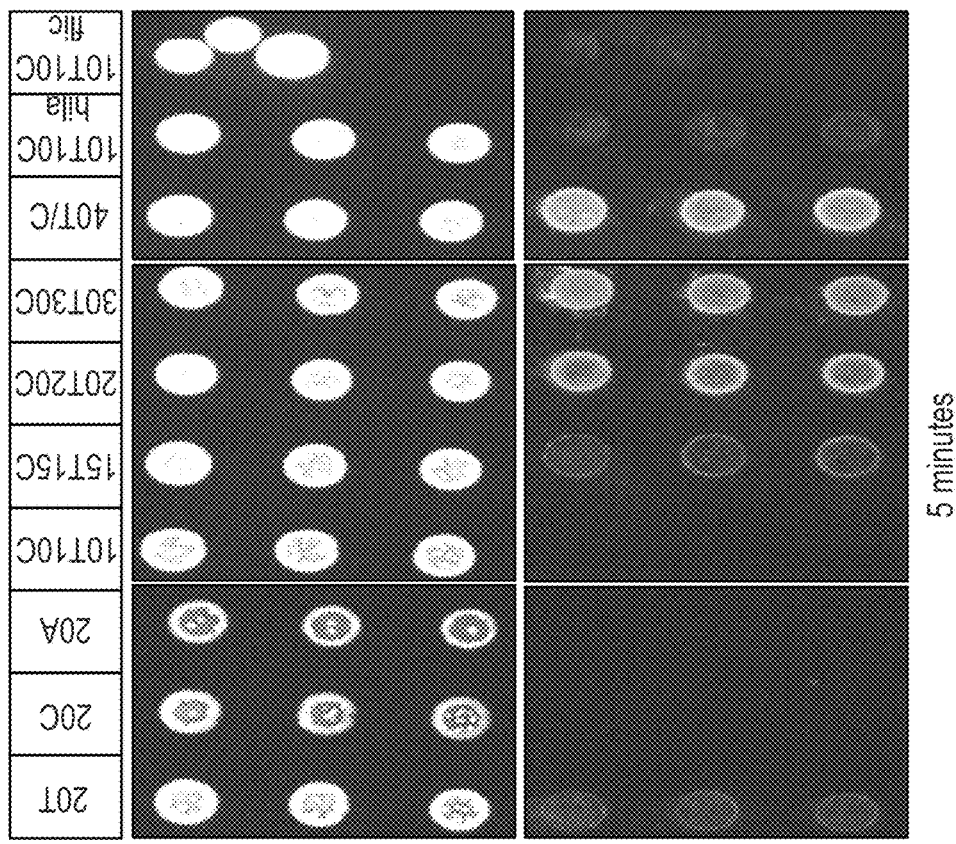
Figure 14B:
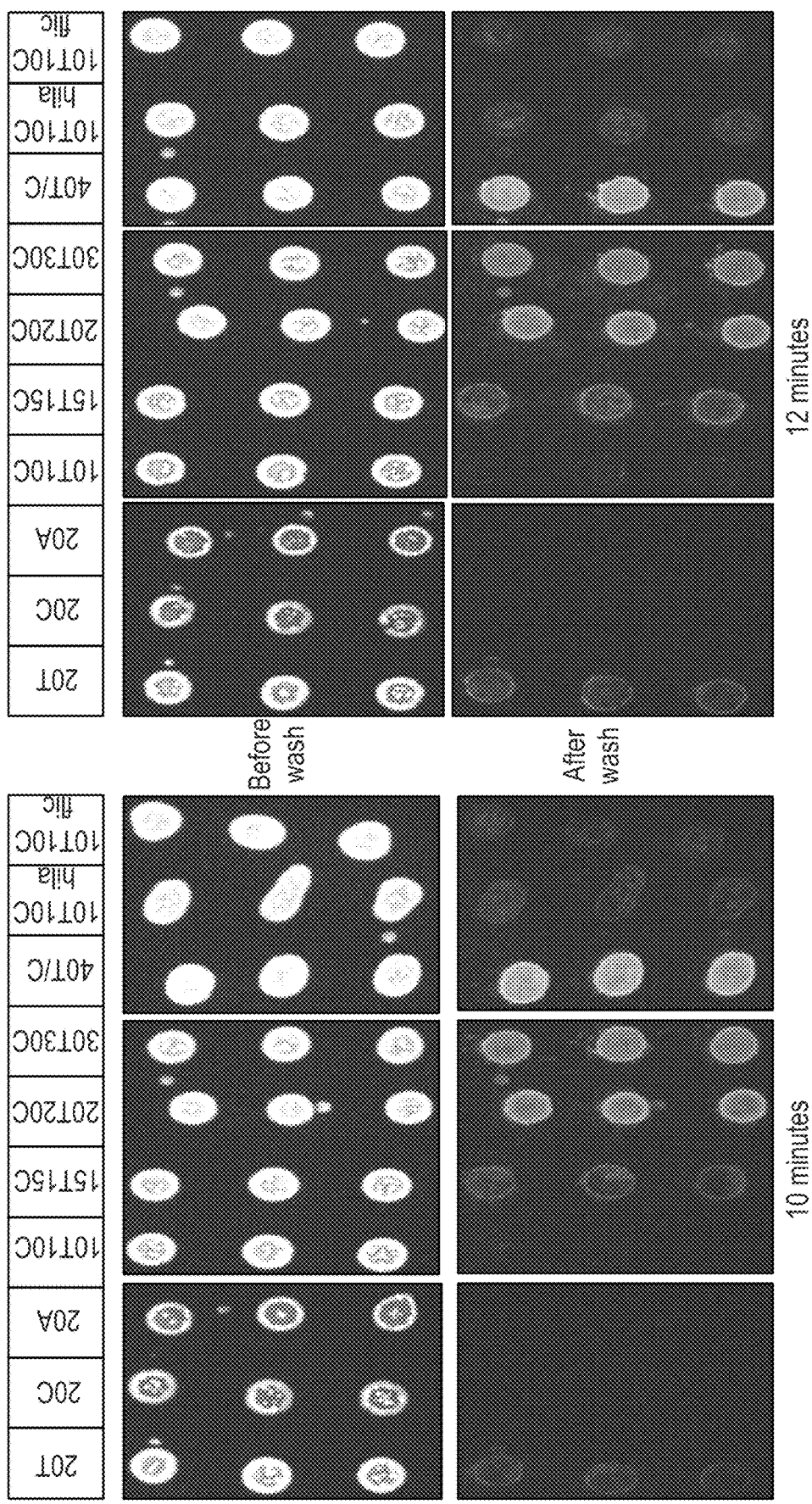
Figure 14C:
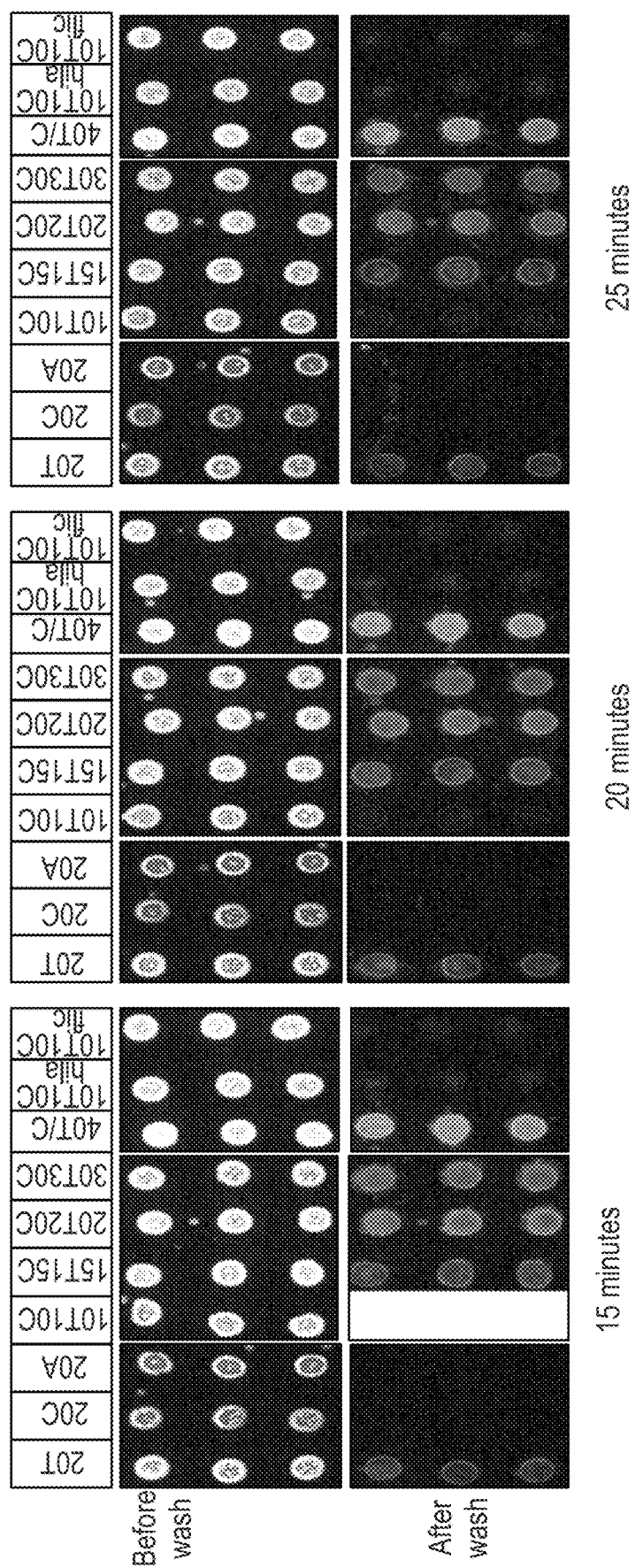

In FIGS. 14a-14c the images of the immobilized polytails obtained at the different UV exposure time before and after wash using the 16 W UV emitter are shown.

EXAMPLE 8

Nucleic acid probes with different length of polytails were tested. The nucleic acid probes comprised the Brtz gene that targets *Bordetella* bacteria.

Figure 15A:
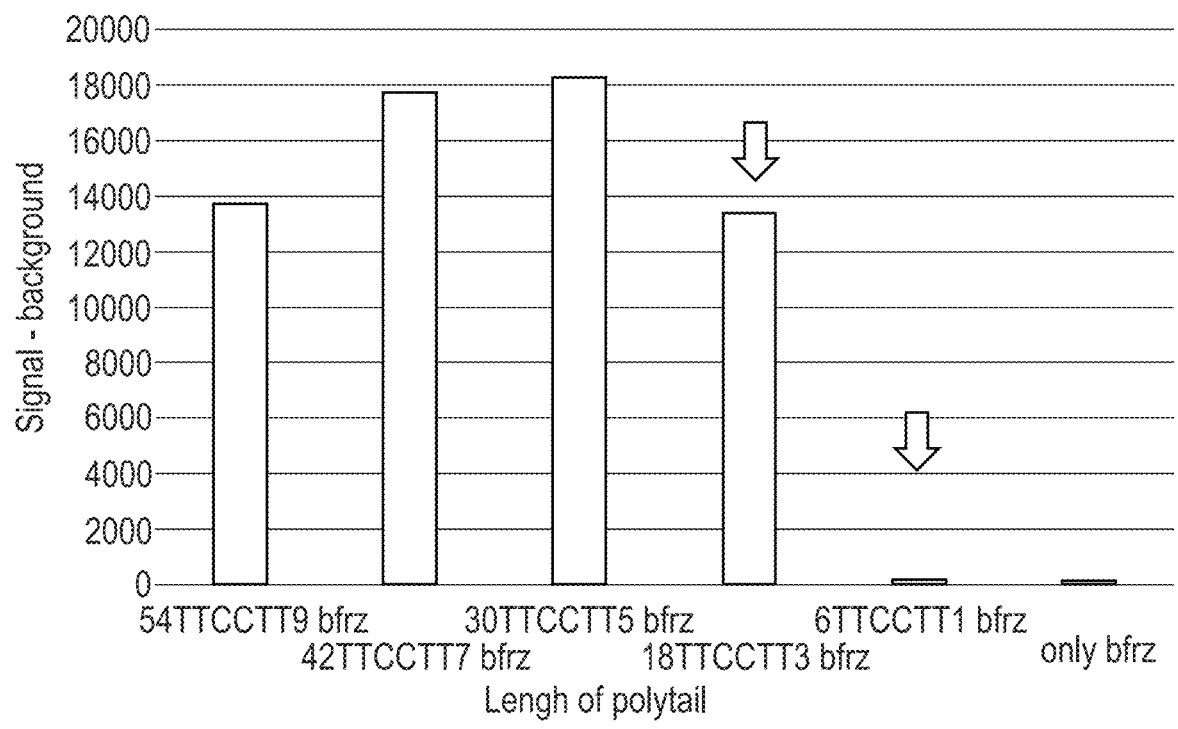
FIG. 15a is diagram showing the signal minus background for a number of marked nucleic acid probes having different polytails.
Figure 15B:
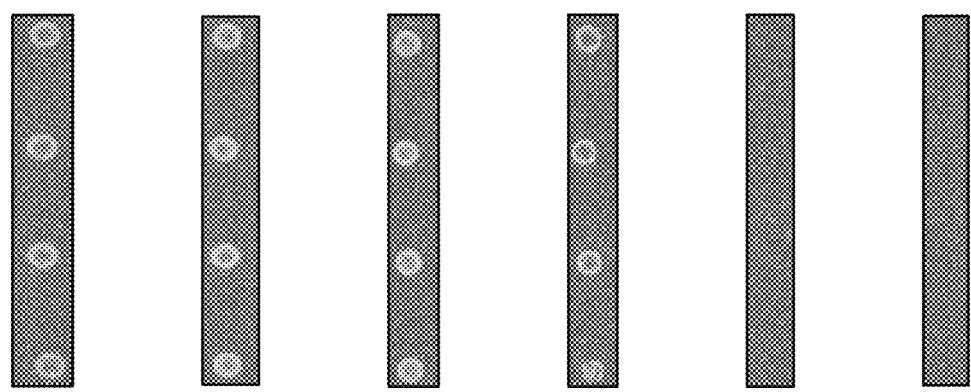

The nucleic acid probes were spotted, immobilized and washed according to the process described in example 1. FIG. 15a show the signal minus background for the various nucleic acid probes. It can be seen that the nucleic acid probes with very short polytails are difficult to immobilize and that nucleic acid probes of embodiments of the invention with polytails of 18 nucleotides or more show an effective immobilization. FIG. 15b are images of the immobilized nucleic acid probes.

EXAMPLE 10

Samples of a nucleic acid probe of an embodiment of the invention having the polytail 42TTCCTT$^7$ (SEQ ID NO:22) and the capture portion that targeting *Bordetella bronchiseptica* bacteria were tested.

The nucleic acid probe samples were spotted, immobilized and washed according to the process described in example 1 but using a different UV exposure time. After the immobilization the samples were subjected to PS-PCR treatment as described in example 2.

Figure 16A:
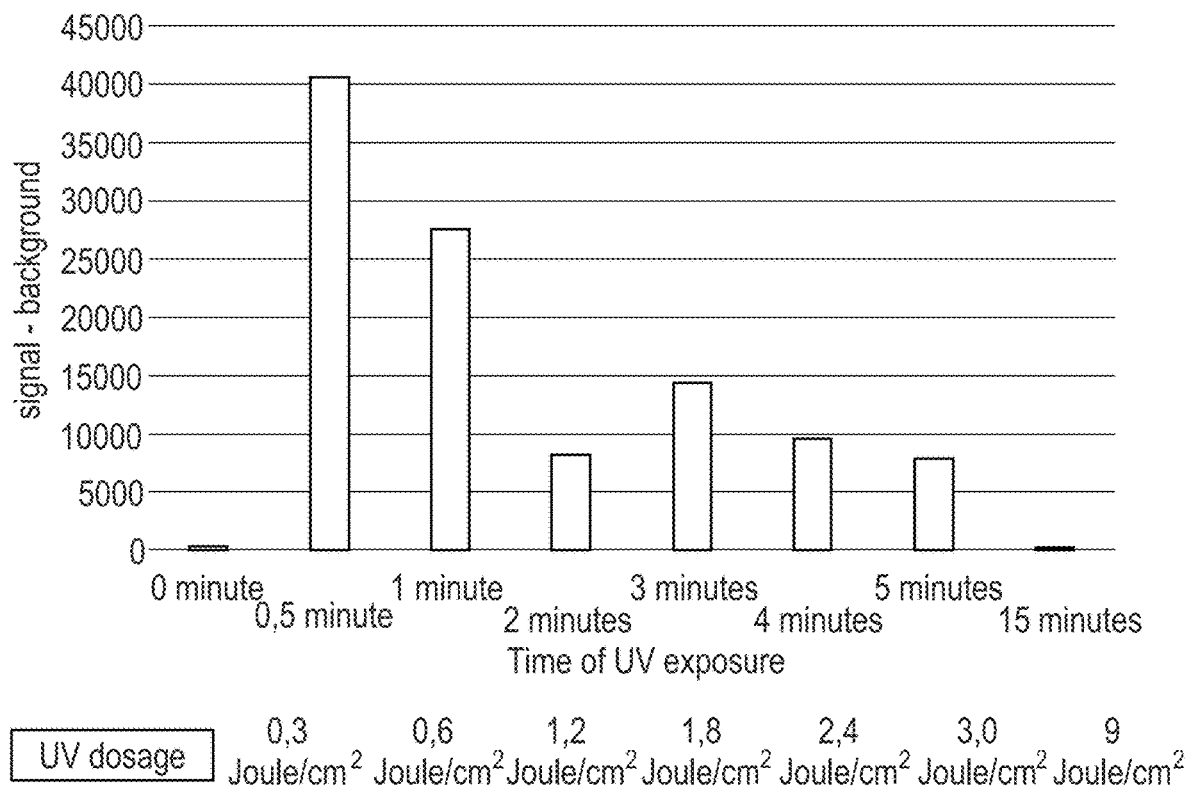
FIG. 16a is diagram showing the signal minus background for a marked nucleic acid probes immobilized to the solid support using different time of UV exposure and thereby UV dosage, where the immobilized nucleic acid probe has been subjected to SP-PCR.

After the PS-PCR treatment the signal minus background signal for each sample were determined. FIG. 16a show the results and it can be seen that an effect immobilization of the nucleic acid probes if embodiments of the invention may be obtained using very low UV dosage.

Figure 16B:
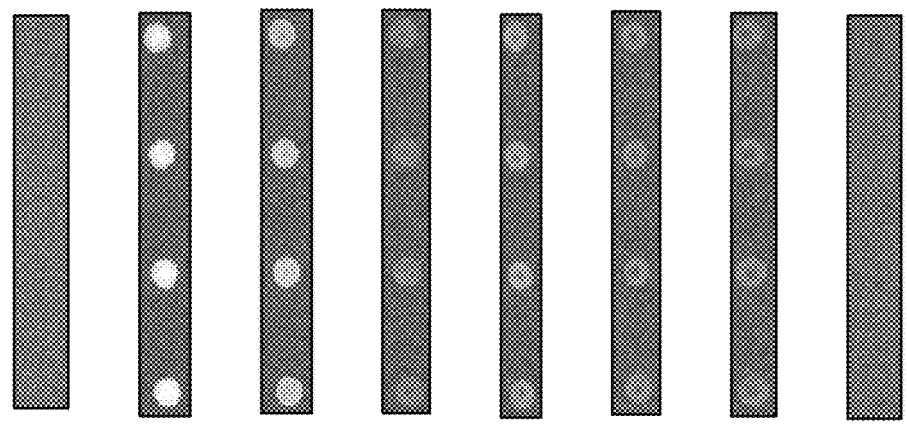
Figure 17:
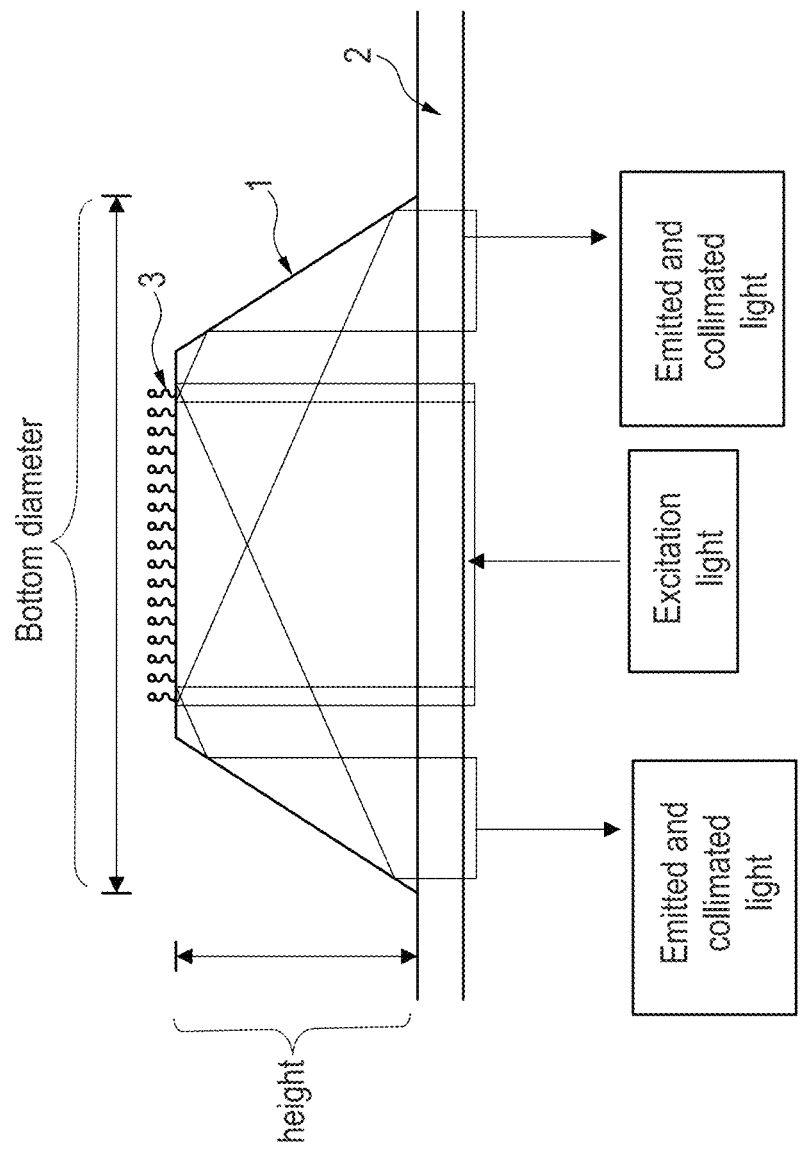
FIG. 17 is a cross-sectional view of a SAF structure comprising immobilized nucleic acid probes.

FIG. 16b are images of the immobilized nucleic acid probes.

The SAF structure 1 corresponds to the SAF structures disclosed in WO17133741 and further details may be found in this document. The SAF structure is mounted to a bottom 2 of a reaction section of a channel of a microfluidic cartridge. The nucleic acid probes 3 marked with fluorophores and of an embodiment of the invention are mounted to a top surface of the SAF structure 1.

The SAF structure 1 has a conical frustum shape with the top surface The SAF structure 1 has a protruding height, a top surface diameter, and a bottom diameter.

The excited fluorophores emit light anisotropically into the SAF structure—which has a higher refractive index than the sample, the air or the liquid in the reaction section—with an angle above a supercritical angle (θc). The emitted light is collimated and can be read out by a reader as a circle of light.

Figure 18:
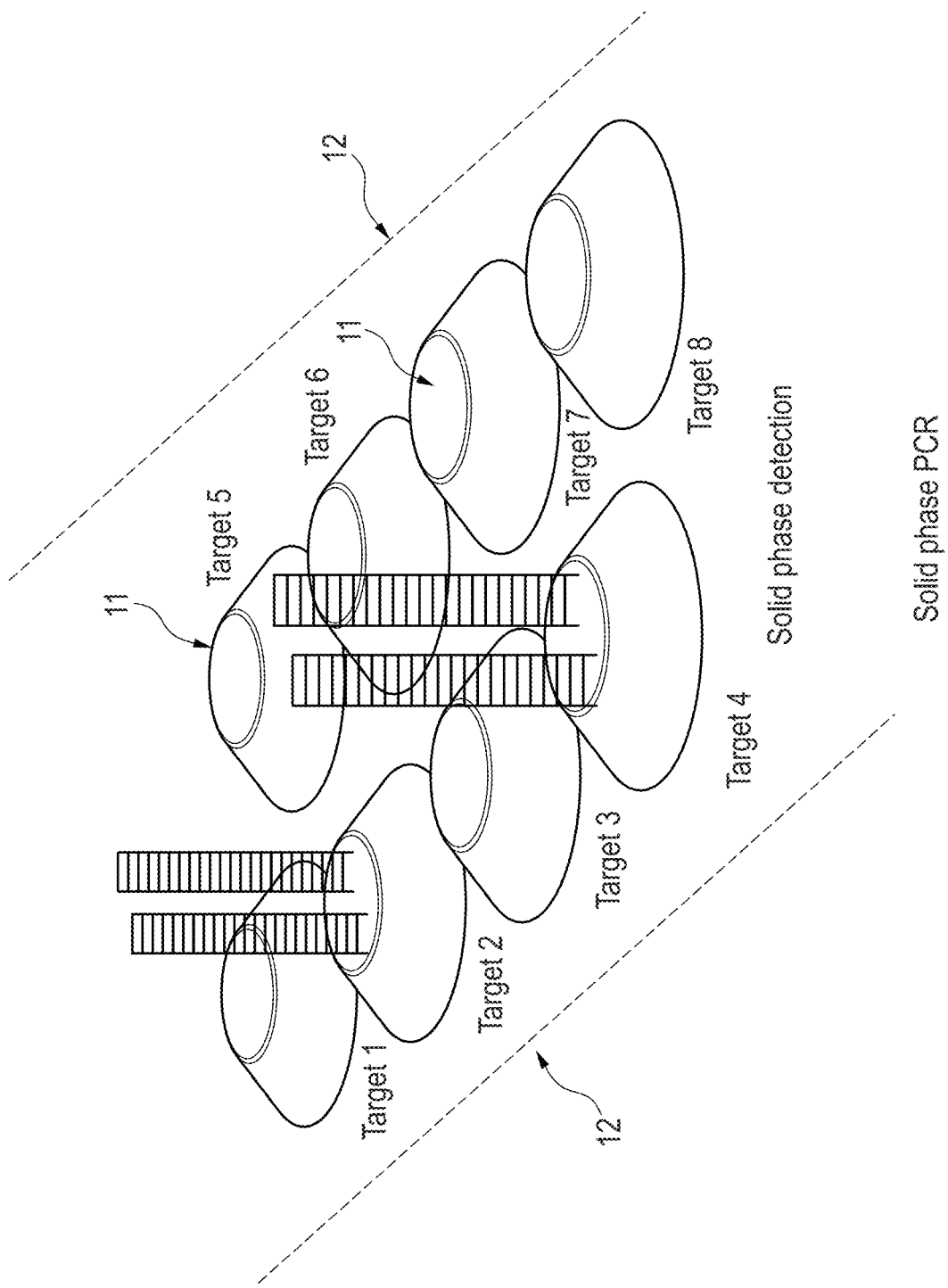
FIG. 18 is a perspective view of a section of a reaction channel of a cartridge, where the reaction section comprises SAP structures with immobilized nucleic acid probes, which have been subjected to SP-CPR.

FIG. 18 is a perspective view of a section of a reaction channel with the edges 12 of a cartridge, where the reaction section comprises SAP structures 11 with immobilized nucleic acid probes, which have been subjected to SP-CPR.

Figure 19:
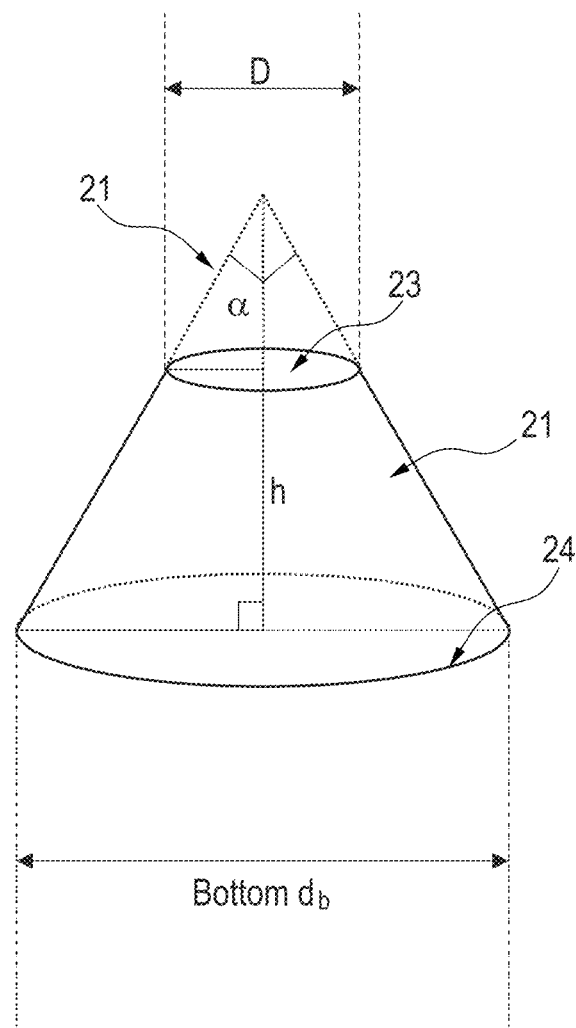
FIG. 19 is a perspective view of a SAF structure illustrated with a dotted top part to show the frustum angle α.

FIG. 19 shows a SAF structure illustrated with a dotted top part to show the frustum angle α. The SAF structure 21 has a bottom periphery 24 where it in mounted to or integrated with the remaining part of the solid support. At its bottom periphery, the SAF structure has a bottom diameter $d_b$. The SAF structure has a top surface 23 with a diameter D. From the bottom to the top surface, the SAF structure has the height h. The illustrated top part is an imaginary top, shown to illustrate the frustum angle.

FIGS. 19a-19d illustrate a standard SAF structure 31, comprising top surface 33. The SAF structure is integrated with a remaining part of the solid support 32. Only some of the remaining part of the solid support is shown. As explained above the solid support may form a cartridge with a channel or it may be a part thereof.

Figure 19A:
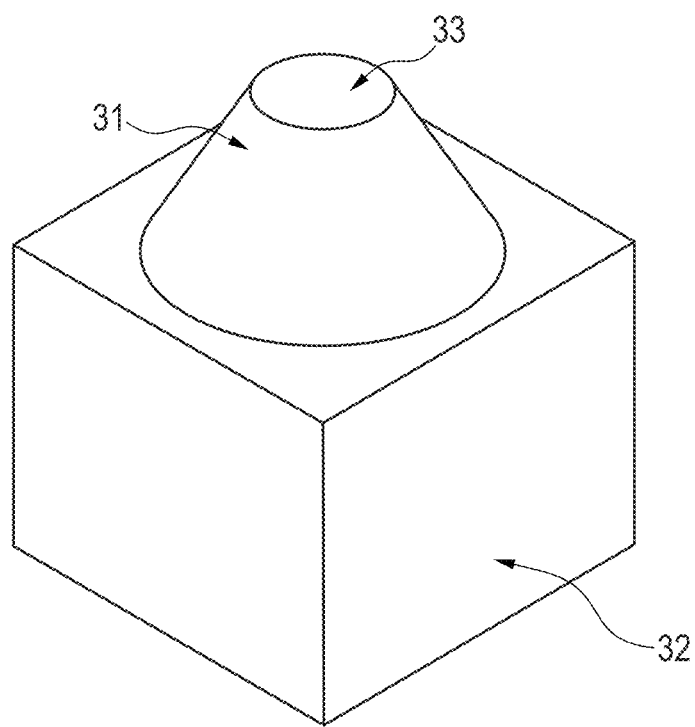
FIGS. 19a-19d illustrate a standard SAF structure with a frustum angle of 60 degrees.
Figure 19B:
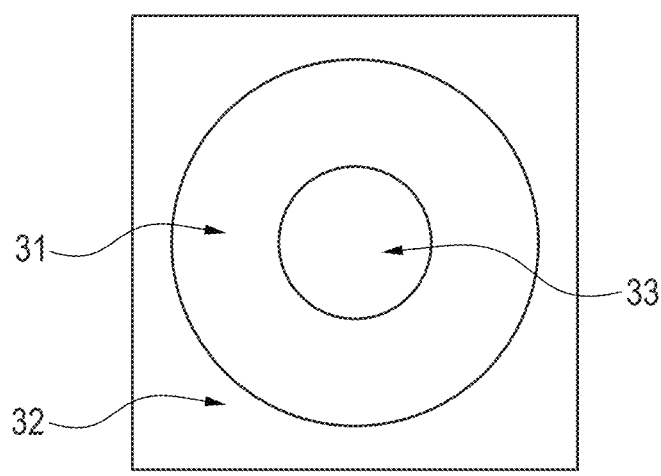
Figure 19C:
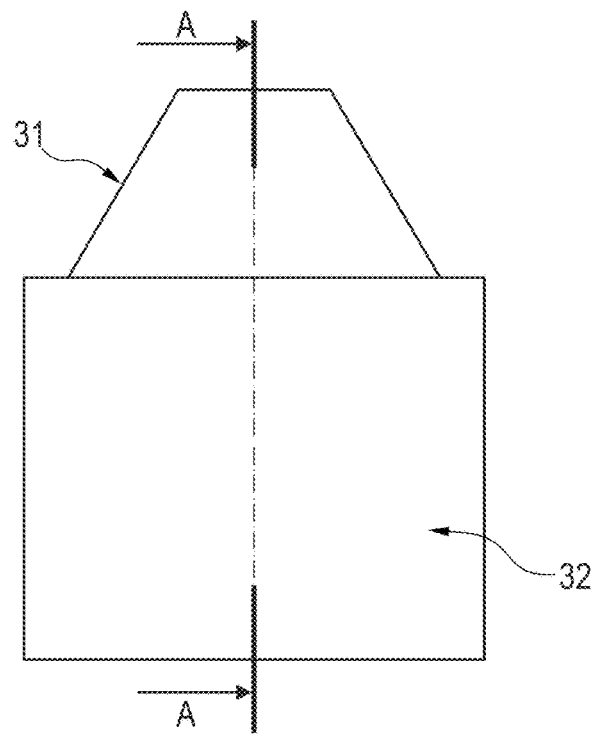
Figure 19D:
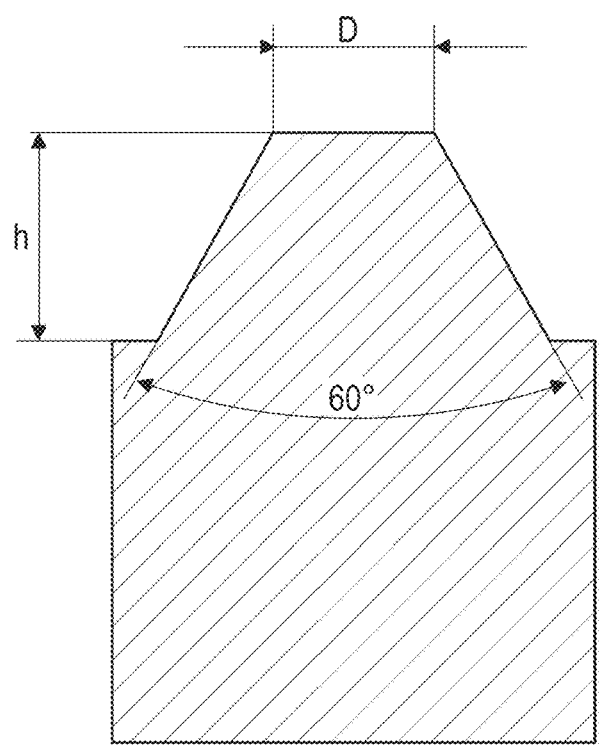

FIG. 19a is a perspective view of the SAF structure 31.
FIG. 19b is a top view of the SAF structure 31.
FIG. 19c is a side view of the SAF structure 31.
FIG. 19d is a cross sectional view of the SAF structure 31 seen in the section A-A of FIG. 19c.

The SAF structure has a height h and a top diameter D. D and h may individually of each other be as disclosed elsewhere herein. The SAF structure 31 is illustrated with a frustum angle of 60 degrees. It should be understood that the SAF structure may have another frustum angle as disclosed elsewhere herein.

It can be seen that the top surface is flat.

In an embodiment, the SAF structure 31 has the following dimensions:

D=0.2 mm; h=0.25 mm and the SAF frustum angle α is 60 degrees.

FIGS. 20a-20d illustrate a preferred SAF structure 41, comprising top surface 43 with a recess 44. The SAF structure is integrated with a remaining part of the solid support 42.

Figure 20A:
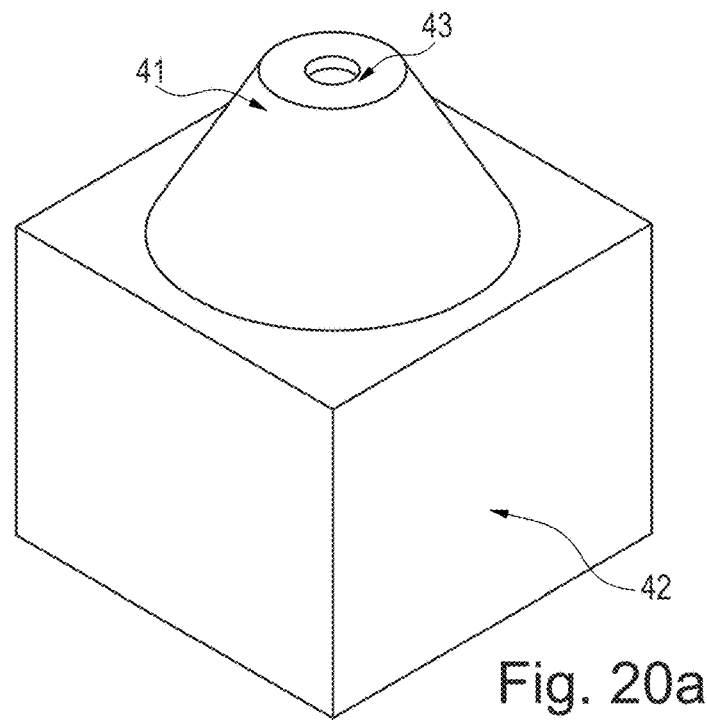
FIGS. 20a-20e show a SAF structure with a top surface recess.
Figure 20B:
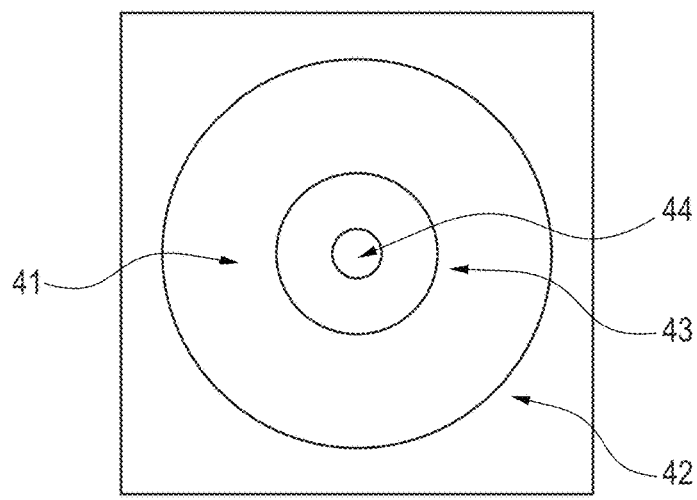

FIG. 20a is a perspective view of the SAF structure 41.
FIG. 20b is a top view of the SAF structure 41.
FIG. 20c is a side view of the SAF structure 41.

Figure 20E:
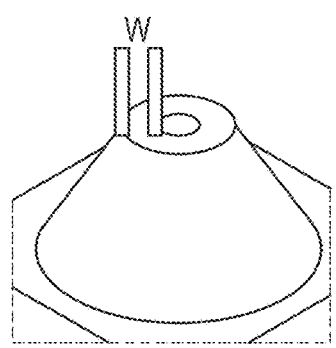
Figure 20C:
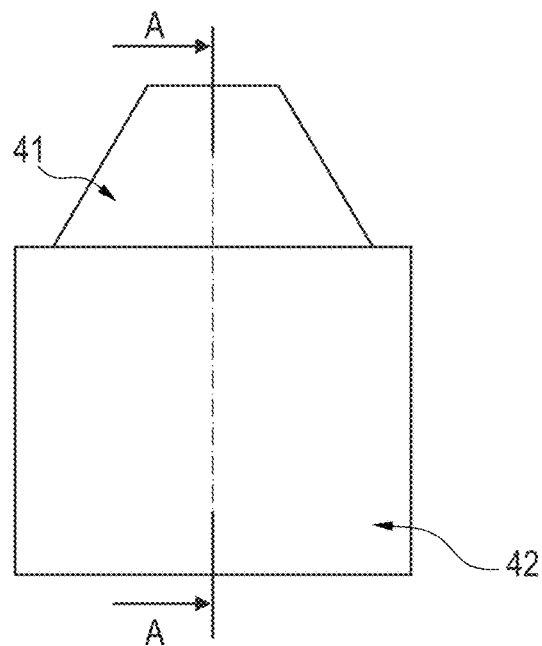
Figure 20D:
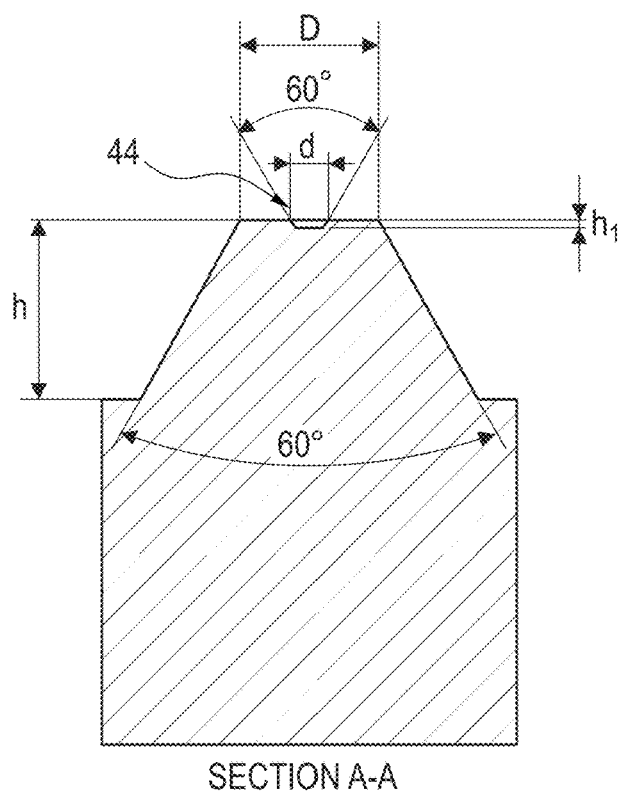

FIG. 20d is a cross sectional view of the SAF structure 41 seen in the section A-A of FIG. 20c.

FIG. 20e show a part of the FIG. 20a, where the recess edge width W is marked. The recess edge width W is advantageously at least about 0.008, such as at least about 0.01, such as at least about 0.015.

The SAF structure has a height h and a top diameter D. D and h may, individually of each other, be as disclosed elsewhere herein. The SAF structure height h is determine from the top surface 43 without the recess 44.

The recess has a height h1, which may be as disclosed elsewhere herein.

The recess is substantially round and is located such that its center axis is coincident with the center axis of the SAF. The recess has a height h1, which may be as disclosed elsewhere herein.

As it can be seen, the recess floor is substantially flat. The recess diameter d is determined at the floor of the recess and may be as disclosed elsewhere herein.

The recess has a conical, frustum shape with a top surface formed by the floor.

In the shown embodiment, the frustum angle θ and the frustum angle α are both 60 degrees. It should be understood that the recess frustum angle θ and the SAF frustum angle α may have other value(s) as disclosed elsewhere herein.

The recess increases the spotting robustness and increase the read out signal intensity.

In an embodiment, the SAF structure 41 has the following dimensions:

D=0.2 mm, h=0.25 mm, d=0.05 mm, h1=0.01 mm, the SAF frustum angle α is 60 degrees and the recess frustum angle θ is 60 degrees.

In another embodiment, the SAF structure 41 has the following dimensions:

D=0.2 mm, h=0.3 mm, d=0.05 mm, h1=0.01 mm, the SAF frustum angle α is 60 degrees and the recess frustum angle θ is 60 degrees.

FIGS. 21a-21d illustrate another preferred SAF structure 51, comprising top surface 53 with a recess 54. The SAF structure is integrated with a remaining part of the solid support 52.

Figure 21A:
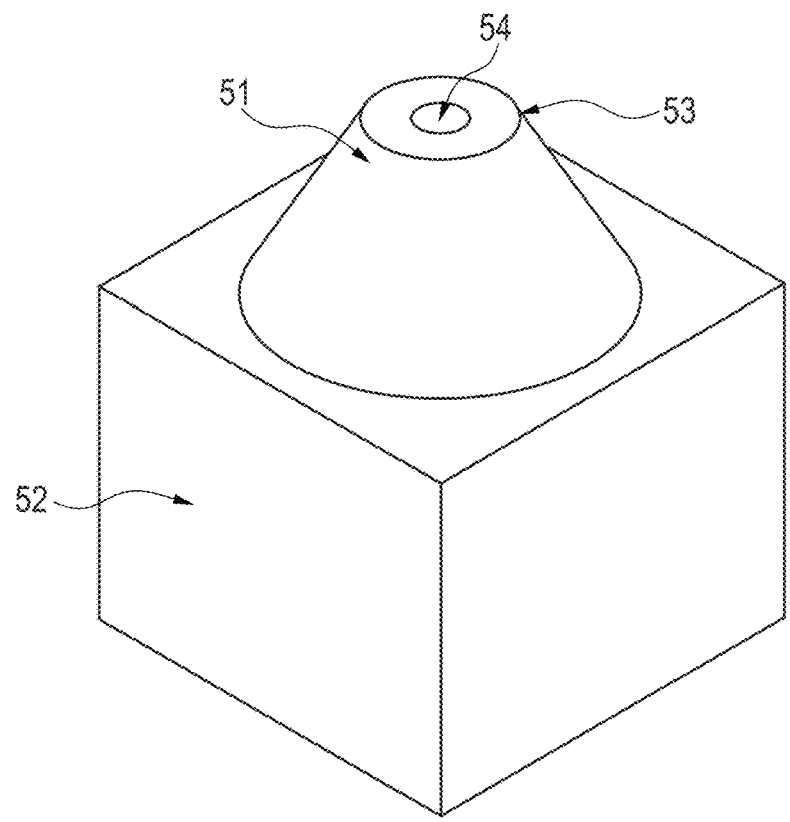
FIGS. 21a-21d show another SAF structure with a top surface recess.

FIG. 21a is a perspective view of the SAF structure 51.

Figure 21B:
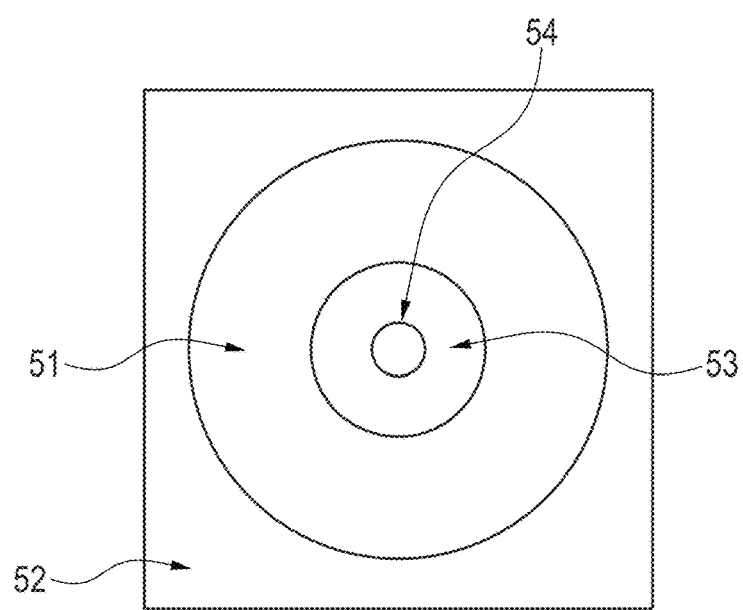

FIG. 21b is a top view of the SAF structure 51.

Figure 21C:
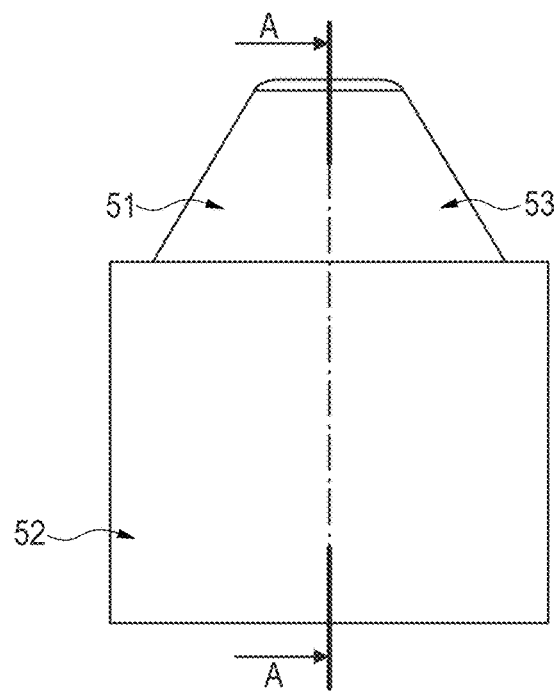

FIG. 21c is a side view of the SAF structure 51.

Figure 21D:
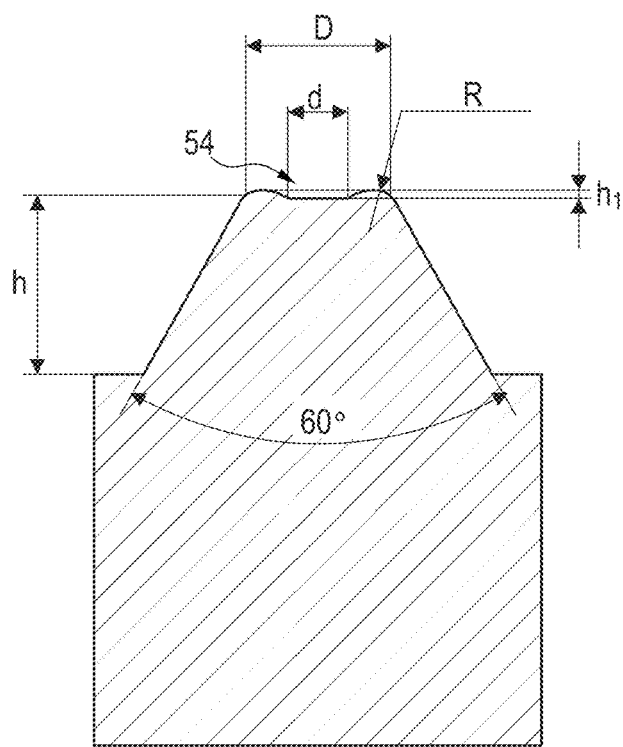

FIG. 21d is a cross sectional view of the SAF structure 51 seen in the section A-A of FIG. 21c.

The SAF structure has a height h and a top diameter D. D and h may, individually of each other, be as disclosed elsewhere herein. The SAF structure height h is determine from the top surface 53 without the recess 54.

The recess 54 has a height h1, which may be as disclosed elsewhere herein.

The recess is substantially round and is located such that its center axis is coincident with the center axis of the SAF. The recess has a height h1, which may be as disclosed elsewhere herein.

As it can be seen, the recess floor is substantially flat. The recess diameter d is determined at the floor of the recess and may be as disclosed elsewhere herein.

The recess has rounded recess edge a rounding radius R, which may be as disclosed elsewhere herein.

In an embodiment, the SAF structure 51 has the following dimensions:

D=0.2 mm; h=0.25 mm, d=0.08 mm, h1=0.01 mm, the recess edge is rounded with a radius R=0.05 mm and the SAF frustum angle α is 60 degrees.

In another embodiment, the SAF structure 51 has the following dimensions:

D=0.2 mm; h=0.3 mm, d=0.08 mm, h1=0.01 mm, the recess edge is rounded with a radius R=0.05 mm and the SAF frustum angle α is 60 degrees.

EXAMPLE 11

Seven cartridges were produced from polystyrene. Each cartridge had a microfluidic channel with a reaction section and eight identical SAF structures protruding from the wall in the reaction section.

Figure 22:
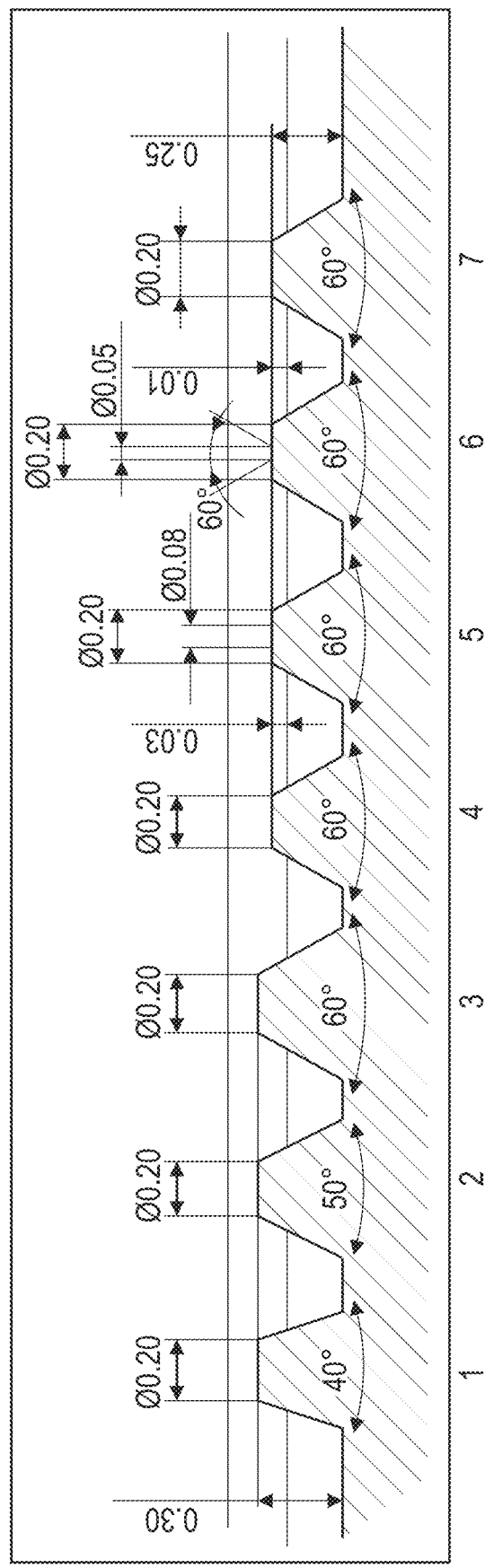
FIG. 22 shows seven different SAF structures used in example 11.

The SAF structures of the first cartridge were shaped as the SAF structure no. 1 in FIG. 22; the structures of the second cartridge were shaped as the SAF structure no. 2 in FIG. 22 and so on.

SAF structure no. 3 was of the type shown in FIGS. 19a-19d.

SAF structure no. 5 was of the type shown in FIGS. 21a-21d and SAF structure no. 6 was of the type shown in FIGS. 20a-20e.

An equal amount of Cy3-labelled oligo was spotted onto the top surface of each of the respective SAF structures and allowed to dry.

In the first test round, the reaction chambers was maintained filled with air. The Cy3-labels were subjected to light at the excitation wavelength (~550 nm) and the signal intensities of the SAF structure emission signals were detected.

For each cartridge, the average SAF structure air/PS interface intensity signal was determined.

In the second test round, the reaction chambers of the respective cartridges were filled with water. The Cy3-labels were subjected to light at the excitation wavelength (~550 nm) and the signal intensities of the SAF structure emission signals were detected.

For each cartridge, the average SAF structure water/PS interface intensity signal was determined.

Figure 23:
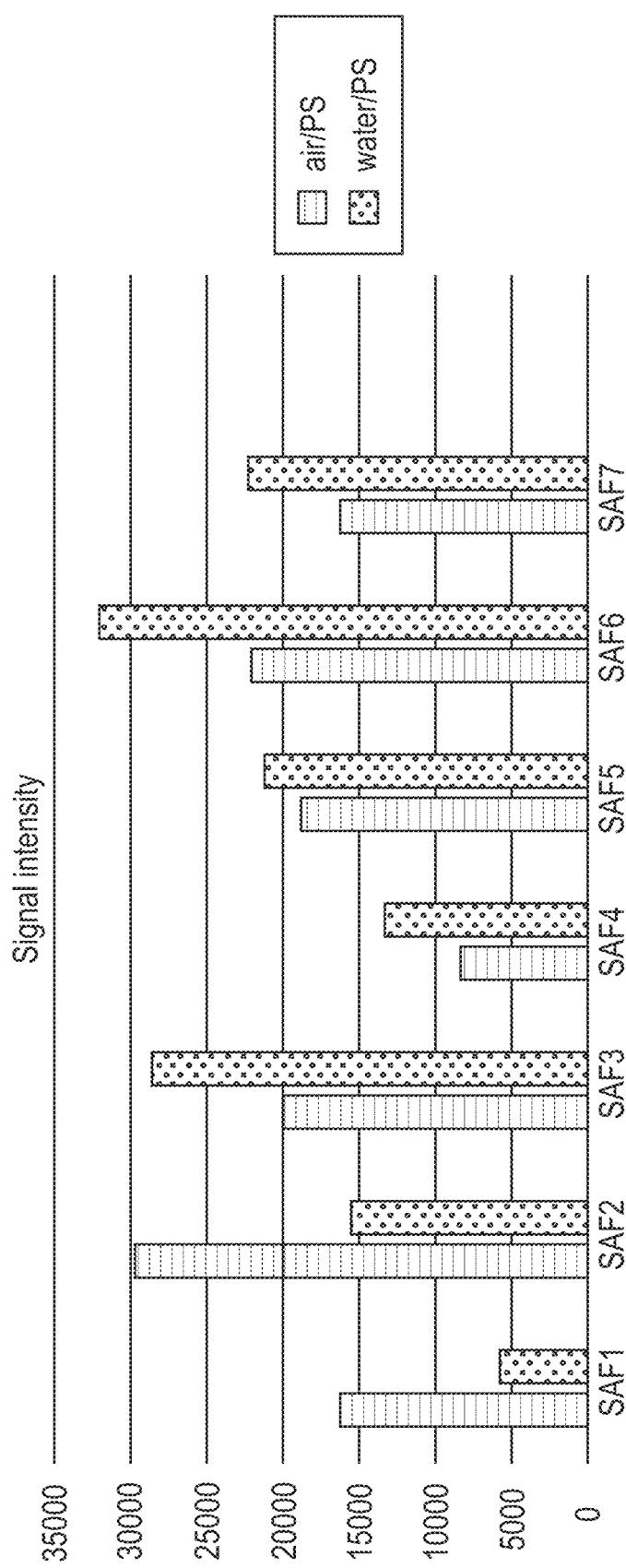
FIG. 23 shows the signal intensity result of example 11.
Figure 24:
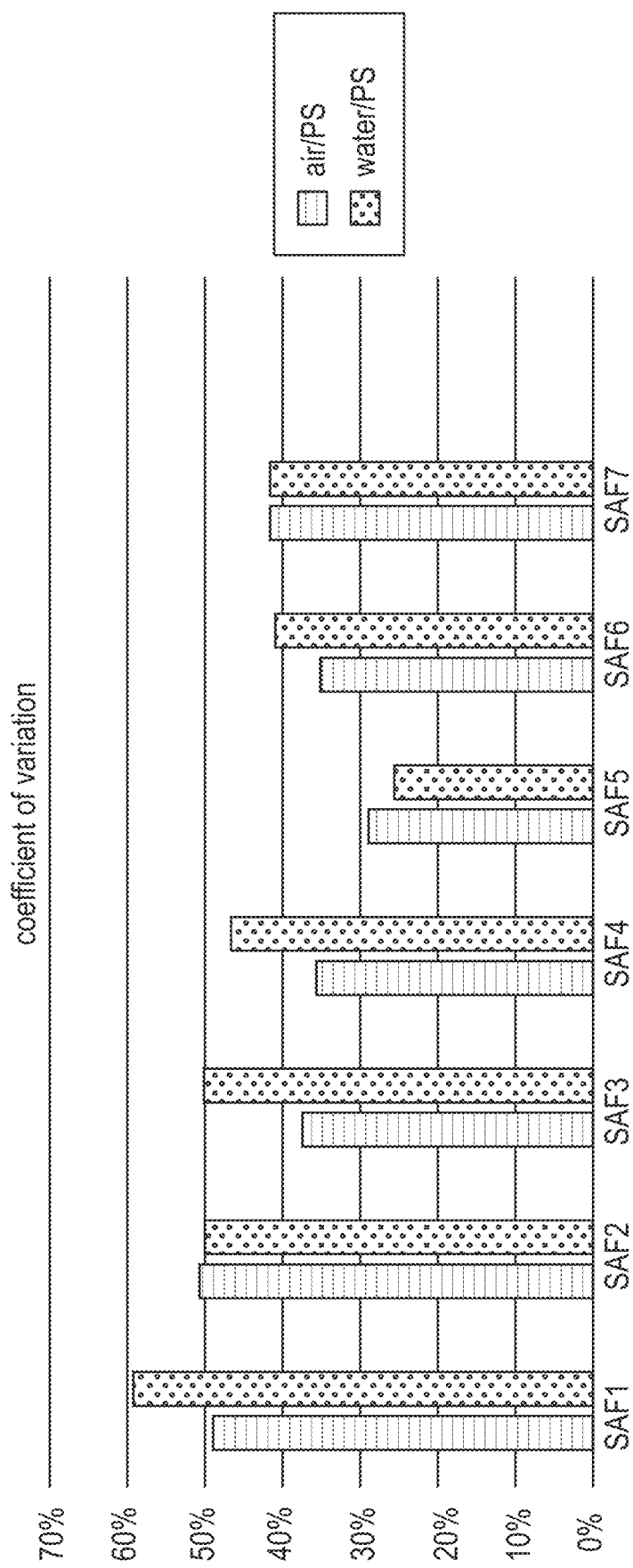
FIG. 24 shows the coefficient of variation result of example 11.

The results are shown in FIG. 23.

The coefficient of variation (CoV) was determined for the SAF structures of the respective cartridges.

It can be seen that the SAF structures nos. 1 and 2 had relatively high light intensities for the air/PS interface signals. Both for the air/PS interface signal intensities and the water/PS interface signals, the CoV were however, relatively high.

The SAF structures no. 6 had the highest light intensity for the water/PS interface signals and the CoV. Both for the air/PS interface signal intensities and the water/PS interface signals, the CoV were however, relatively high.

The CoV for sample 6 was however relatively high. It is believed that the reason for this relatively high CoV is that the some of the SAF structures at their bottom periphery where they are integrated with the remaining solid support, had small surface corrugations and/or protrusions, which may result in loss of signal. Hence, it is expected that by decreasing the top diameter to height aspect ratio D/h, this possibly loss of light signal may be mitigated. It is believed that by increasing the height e.g. to about 0.3 mm, the signal may be increased and the CoV may be decreased.

The SAF structures no. 5 had both a highest light intensity and a low CoV for the water/PS interface signals.

It is believed that the rounded edges of the recess ensure a very effective and robust spotting, which add to the low CoV.

The SAF structures no. 6 had the highest light intensity for the water/PS interface signals and the CoV. Both for the air/PS interface signal intensities and the water/PS interface signals, the CoV were however, relatively high.

The invention claimed is:

1. A method of immobilizing a nucleic acid probe to a solid support, the method comprising
providing the nucleic acid probe to comprise a terminus anchor chain portion, and a capture portion
applying the nucleic acid probe onto a surface of the solid support, and
anchoring only the anchor chain portion of the nucleic acid probe to the solid support by subjecting it to UV light,
wherein the terminus anchor chain portion of the nucleic acid probe comprises a sequence of N nucleotides composed of at least two stretches of nucleotides of base type X with intermediate nucleotide(s) of base type Cytosine (C) and optionally one nucleotide of base type Guanine (G) between said stretches of base type X or a sequence with at least 90% similarity thereto of said sequence of N nucleotides, wherein the stretches of nucleotides of base type X independently of each other are at least 1 and no more than 5 nucleotides, wherein N is at least 18 and wherein each base type X independently of each other designate base type Thymine (T) or base type Uracil (U), wherein % similarity=100*(N−n)/N, wherein n is the number n of nucleotides in the sequence of N nucleotides which differs from the composition of the stretches of nucleotides of base type X with intermediate nucleotide(s) of base type C.

2. The method of claim 1, wherein the sequence of N nucleotides comprises less than 5% of nucleotides with purine nucleobases.

3. The method of claim 1, wherein the terminus anchor chain portion of the nucleic acid probe comprises a sequence of at least N nucleotides composed of at least two stretches of from 2 to 5 nucleotides of base type X with intermediate nucleotide(s) of base type C and wherein N is at least 20.

4. The method of claim 1, wherein the sequence of N nucleotides comprises repeating sub-sequences of nucleotides of base types according to the formula $$(-(X)_Y-(C)_Z-)_M,$$

wherein Y is an integer from 1 to 5, Z is an integer from 1 to 5, Y≥Z and M is an integer from 4 to 20.

5. The method of claim 4, wherein Y is an integer from 2 to 5, Z is an integer from 1 to 4, Y>Z and M is an integer from 4 to 20.

6. The method of claim 1, wherein the sequence of N nucleotides comprises repeating sub-sequences of nucleotides of base types according to the formula $$(-(X)_{Y2}-(C)_Z-(X)_{Y2}-)_M,$$

wherein $Y_2$ is an integer from 1 to 4, Z is an integer from 1 to 4, and M is an integer from 4 to 20.

7. The method of claim 6, wherein $Y_2$ is an integer from 2 to 3, Z is an integer from 1 to 3.

8. The method of claim 1, wherein the capture portion comprises a primer and/or a hybridization chain portion comprising a sequence of nucleotides adapted to hybridize to a complementary region of a target nucleic acid probe and/or adapted for performing a Polymerase Chain Reaction (PCR) assay.

9. The method of claim 1, wherein the nucleic acid probe is deposited onto the surface of the solid support by spotting.

10. The method of claim 1, wherein at least the surface of the solid support is a polystyrene PS surface.

11. The method of claim 1, wherein the solid support surface is essentially free of one or more of amine groups, methylene groups, thiol groups, epoxy groups, diazo groups or amide groups.

12. The method of claim 1, wherein the solid support is at least a part of a cartridge comprising a channel with a channel surface defining the channel, wherein the surface of the solid substrate forms at least a part of the channel surface and wherein the channel comprises a reaction section, wherein said nucleic acid probe immobilizes onto a surface within the reaction section of the channel.

13. The method of claim 12, wherein the reaction section comprises at least one optical element, wherein said optical element comprises a lens structure and/or a supercritical angle fluorescence structure (SAF structure), said SAF structure has a top surface, wherein said nucleic acid probe immobilizes onto said top surface.

14. A method of immobilizing a nucleic acid probe to a solid support, the method comprising
providing the nucleic acid probe, wherein the nucleic acid probe comprises a terminus anchor chain portion and a capture portion,
applying the nucleic acid probe onto a surface of the solid support, and
anchoring the anchor chain portion of the nucleic acid probe to the solid support by subjecting it to UV light,
wherein the terminus anchor chain portion of the nucleic acid probe comprises a sequence of N nucleotides composed of at least two stretches of nucleotides of base type X with intermediate nucleotide(s) of base type Cytosine (C) and optionally one nucleotide of base type Guanine (G) between said stretches of base type X or a sequence with at least 90% similarity thereto of said sequence of N nucleotides, wherein the stretches of nucleotides of base type X independently of each other are at least 1 and no more than 5 nucleotides, wherein N is at least 18 and wherein each base type X independently of each other designate base type Thymine (T) or base type Uracil (U), wherein % similarity=100*(N−n)/N, wherein n is the number n of nucleotides in the sequence of N nucleotides which differs from the composition of the stretches of nucleotides of base type X with intermediate nucleotide(s) of base type C,
wherein the solid support is at least a part of a cartridge comprising a channel with a channel surface defining the channel, wherein the surface of the solid substrate forms at least a part of the channel surface and wherein the channel comprises a reaction section, wherein said nucleic acid probe immobilizes onto a surface within the reaction section of the channel,
wherein the reaction section comprises at least one optical element, wherein said optical element comprises a lens structure and/or a supercritical angle fluorescence structure (SAF structure), said SAF structure has a top surface, wherein said nucleic acid probe immobilizes onto said top surface,
wherein the optical element has a SAF structure with a conical, frustum shape with a frustum angle α, a top surface, a top diameter D and a height h, wherein the frustum angle α is from about 30° to about 70°, the top diameter to height aspect ratio D/h which is about 1.1 or less and the SAF structure comprises a top surface recess.

15. The method of claim 1, wherein the anchor chain portion of the nucleic acid is anchored to the solid support by subjecting it to UV light comprising a wavelength in the range of from about 250 nm to 500 nm.

16. The method of claim 1, wherein the anchor chain portion of the nucleic acid is anchored to the solid support by subjecting it to UV light using an amount of energy from about 0.2 Joule/cm² to about 15 Joule/cm².

17. A solid support comprising a surface carrying dried nucleic acid probe, the nucleic acid probe comprising a terminus anchor chain portion, and a capture portion, wherein the terminus anchor chain portion of the nucleic acid probe comprises a sequence of N nucleotides composed of at least two stretches of nucleotides of base type X with intermediate nucleotide(s) of base type Cytosine (C) between said stretches of base type X or a sequence with at least 90% similarity thereto of said sequence of N nucleotides, wherein the stretches of nucleotides of base type X independently of each other are at least 2 and no more than 5 nucleotides, wherein N is at least 18 and wherein each base type X independently of each other designate base type Thymine (T) or base type Uracil (U), wherein % similarity=100*(N−n)/N, wherein n is the number n of nucleotides in the sequence of N nucleotides which differs from the composition of the stretches of nucleotides of base type X with intermediate nucleotide(s) of base type C, wherein only the terminal anchor portion is photochemically anchored to the solid support.

18. The suspension of claim 17, wherein the terminus anchor chain portion of the nucleic acid probe comprises a sequence of at least N nucleotides composed of at least two stretches of from 2 to 5 nucleotides of base type X with intermediate nucleotide(s) of base type C.

19. The suspension of claim 17, wherein the sequence of N nucleotides of the terminus anchor chain portion of the nucleic acid probe comprises repeating sub-sequences of nucleotides of base types according to the formula $$(-(X)_Y-(C)_Z-)_M,$$

wherein Y is an integer from 1 to 5, Z is an integer from 1 to 5, Y≥Z and M is an integer from 4 to 20.

20. The suspension of claim 19, wherein
Y=2 and M≥10
or
Y=3 and M≥6
or
Y=4 and M≥4.

21. The suspension of claim 17, wherein the sequence of N nucleotides of the terminus anchor chain portion of the nucleic acid probe comprises repeating sub-sequences of nucleotides of base types according to the formula $$(-(X)_{Y2}-(C)_Z-(X)_{Y2}-)_M,$$

wherein Y2 is an integer from 2 to 4, Z is an integer from 1 to 4, and M is an integer from 4 to 20.

22. The suspension of claim 21, wherein
$Y_2$=2 and M≥10
or
$Y_2$=3 and M≥4.

23. The suspension of claim 17, wherein the capture portion comprises a chain of nucleotides having from about 4 to about 100 nucleotides.

24. A solid support comprising an immobilized nucleic acid probe, the nucleic acid probe comprising a terminus anchor chain portion, and a capture portion, wherein the terminus anchor chain portion of the nucleic acid probe comprises a sequence of N nucleotides composed of at least two stretches of nucleotides of base type X with intermediate nucleotide(s) of base type Cytosine (C) between said stretches of base type X or a sequence with at least 90% similarity thereto of said sequence of N nucleotides, wherein the stretches of nucleotides of base type X independently of each other are at least 2 and no more than 5 nucleotides, wherein N is at least 18 and wherein each base type X independently of each other designate base type Thymine (T) or base type Uracil (U), wherein % similarity=100*(N−n)/N, wherein n is the number n of nucleotides in the sequence of N nucleotides which differs from the composition of the stretches of nucleotides of base type X with intermediate nucleotide(s) of base type C, wherein only the terminal anchor portion is photochemically anchored to the solid support.

* * * * *

SEQUENCE LISTING

<160> NUMBER OF SEQ ID NOS: 35

<210> SEQ ID NO 1
<211> LENGTH: 20
<212> TYPE: DNA
<213> ORGANISM: Artificial Sequence
<220> FEATURE:
<223> OTHER INFORMATION: Probe

<400> SEQUENCE: 1
tttttttttt cccccccccc                                               20

<210> SEQ ID NO 2
<211> LENGTH: 30
<212> TYPE: DNA
<213> ORGANISM: Artificial Sequence
<220> FEATURE:
<223> OTHER INFORMATION: Probe

<400> SEQUENCE: 2
tttttttttt tttttccccc cccccccccc                                    30

<210> SEQ ID NO 3
<211> LENGTH: 40
<212> TYPE: DNA
<213> ORGANISM: Artificial Sequence
<220> FEATURE:
<223> OTHER INFORMATION: Probe

<400> SEQUENCE: 3
tttttttttt tttttttttt cccccccccc cccccccccc                         40

<210> SEQ ID NO 4
<211> LENGTH: 60
<212> TYPE: DNA
<213> ORGANISM: Artificial Sequence
<220> FEATURE:
<223> OTHER INFORMATION: Probe

<400> SEQUENCE: 4
tttttttttt tttttttttt tttttttttt cccccccccc cccccccccc cccccccccc   60

<210> SEQ ID NO 5
<211> LENGTH: 40
<212> TYPE: DNA
<213> ORGANISM: Artificial Sequence
<220> FEATURE:
<223> OTHER INFORMATION: Probe

<400> SEQUENCE: 5
tctctctctc tctctctctc tctctctctc tctctctctc                         40

<210> SEQ ID NO 6
<211> LENGTH: 20
<212> TYPE: DNA
<213> ORGANISM: Artificial Sequence
<220> FEATURE:
<223> OTHER INFORMATION: Probe

<400> SEQUENCE: 6
tttttttttt tttttttttt                                               20

<210> SEQ ID NO 7
<211> LENGTH: 80
<212> TYPE: DNA
<213> ORGANISM: Artificial Sequence

```
<220> FEATURE:
<223> OTHER INFORMATION: Probe

<400> SEQUENCE: 7 ttttttttttt cccccccccc cggtttaatc gtccggtcgt agtggtgtct ccgccagcgc    60
cgcaacctac gactcataca                                                 80

<210> SEQ ID NO 8
<211> LENGTH: 80
<212> TYPE: DNA
<213> ORGANISM: Artificial Sequence
<220> FEATURE:
<223> OTHER INFORMATION: Probe

<400> SEQUENCE: 8 ttttttttttt cccccccccc acttacgctg caagtaaagc cgaaggtcac aactttaaag    60
cacagcctga tctggcggaa                                                 80

<210> SEQ ID NO 9
<211> LENGTH: 20
<212> TYPE: DNA
<213> ORGANISM: Artificial Sequence
<220> FEATURE:
<223> OTHER INFORMATION: Probe

<400> SEQUENCE: 9
cccccccccc cccccccccc                                                 20

<210> SEQ ID NO 10
<211> LENGTH: 20
<212> TYPE: DNA
<213> ORGANISM: Artificial Sequence
<220> FEATURE:
<223> OTHER INFORMATION: Probe

<400> SEQUENCE: 10
aaaaaaaaaa aaaaaaaaaa                                                 20

<210> SEQ ID NO 11
<211> LENGTH: 20
<212> TYPE: DNA
<213> ORGANISM: Artificial Sequence
<220> FEATURE:
<223> OTHER INFORMATION: Probe

<400> SEQUENCE: 11
gggggggggg gggggggggg                                                 20

<210> SEQ ID NO 12
<211> LENGTH: 40
<212> TYPE: DNA
<213> ORGANISM: Artificial Sequence
<220> FEATURE:
<223> OTHER INFORMATION: Probe

<400> SEQUENCE: 12
ctctctctct ctctctctct ctctctctct ctctctctct                           40

<210> SEQ ID NO 13
<211> LENGTH: 40
<212> TYPE: DNA
<213> ORGANISM: Artificial Sequence
<220> FEATURE:
<223> OTHER INFORMATION: Probe
```

<400> SEQUENCE: 13
ttccttcctt ccttccttcc ttccttcctt ccttccttcc                                    40

<210> SEQ ID NO 14
<211> LENGTH: 42
<212> TYPE: DNA
<213> ORGANISM: Artificial Sequence
<220> FEATURE:
<223> OTHER INFORMATION: Probe

<400> SEQUENCE: 14 tttcccttc cctttccctt tccctttccc tttcccttc cc                                   42

<210> SEQ ID NO 15
<211> LENGTH: 40
<212> TYPE: DNA
<213> ORGANISM: Artificial Sequence
<220> FEATURE:
<223> OTHER INFORMATION: Probe

<400> SEQUENCE: 15
ttttcccctt ttcccctttt ccccttttcc ccttttcccc                                    40

<210> SEQ ID NO 16
<211> LENGTH: 42
<212> TYPE: DNA
<213> ORGANISM: Artificial Sequence
<220> FEATURE:
<223> OTHER INFORMATION: Probe

<400> SEQUENCE: 16
ttcttcttct tcttcttctt cttcttcttc ttcttcttct tc                                 42

<210> SEQ ID NO 17
<211> LENGTH: 40
<212> TYPE: DNA
<213> ORGANISM: Artificial Sequence
<220> FEATURE:
<223> OTHER INFORMATION: Probe

<400> SEQUENCE: 17
tttctttctt tctttctttc tttctttctt tctttctttc                                    40

<210> SEQ ID NO 18
<211> LENGTH: 40
<212> TYPE: DNA
<213> ORGANISM: Artificial Sequence
<220> FEATURE:
<223> OTHER INFORMATION: Probe

<400> SEQUENCE: 18
ttttcttttc ttttcttttc ttttcttttc ttttcttttc                                    40

<210> SEQ ID NO 19
<211> LENGTH: 39
<212> TYPE: DNA
<213> ORGANISM: Artificial Sequence
<220> FEATURE:
<223> OTHER INFORMATION: Probe

<400> SEQUENCE: 19
tcctcctcct cctcctcctc ctcctcctcc tcctcctcc                                     39

<210> SEQ ID NO 20
<211> LENGTH: 40
<212> TYPE: DNA
<213> ORGANISM: Artificial Sequence
<220> FEATURE:
<223> OTHER INFORMATION: Probe

<400> SEQUENCE: 20
tccctccctc cctccctccc tccctccctc cctccctccc                            40

<210> SEQ ID NO 21
<211> LENGTH: 39
<212> TYPE: DNA
<213> ORGANISM: Artificial Sequence
<220> FEATURE:
<223> OTHER INFORMATION: Probe

<400> SEQUENCE: 21
tcttcttctt cttcttcttc ttcttcttct tcttcttct                             39

<210> SEQ ID NO 22
<211> LENGTH: 42
<212> TYPE: DNA
<213> ORGANISM: Artificial Sequence
<220> FEATURE:
<223> OTHER INFORMATION: Probe

<400> SEQUENCE: 22
ttccttttcc ttttcctttt cctttcctt ttccttttcc tt                          42

<210> SEQ ID NO 23
<211> LENGTH: 40
<212> TYPE: DNA
<213> ORGANISM: Artificial Sequence
<220> FEATURE:
<223> OTHER INFORMATION: Probe

<400> SEQUENCE: 23
tatatatata tatatatata tatatatata tatatatata                            40

<210> SEQ ID NO 24
<211> LENGTH: 40
<212> TYPE: DNA
<213> ORGANISM: Artificial Sequence
<220> FEATURE:
<223> OTHER INFORMATION: Probe

<400> SEQUENCE: 24
tgtgtgtgtg tgtgtgtgtg tgtgtgtgtg tgtgtgtgtg                            40

<210> SEQ ID NO 25
<211> LENGTH: 40
<212> TYPE: DNA
<213> ORGANISM: Artificial Sequence
<220> FEATURE:
<223> OTHER INFORMATION: Probe

<400> SEQUENCE: 25
agagagagag agagagagag agagagagag agagagagag                            40

<210> SEQ ID NO 26
<211> LENGTH: 40
<212> TYPE: DNA
<213> ORGANISM: Artificial Sequence
<220> FEATURE:
<223> OTHER INFORMATION: Probe

```
<400> SEQUENCE: 26
gcgcgcgcgc gcgcgcgcgc gcgcgcgcgc gcgcgcgcgc                           40

<210> SEQ ID NO 27
<211> LENGTH: 40
<212> TYPE: DNA
<213> ORGANISM: Artificial Sequence
<220> FEATURE:
<223> OTHER INFORMATION: Probe

<400> SEQUENCE: 27
acacacacac acacacacac acacacacac acacacacac                           40

<210> SEQ ID NO 28
<211> LENGTH: 39
<212> TYPE: DNA
<213> ORGANISM: Artificial Sequence
<220> FEATURE:
<223> OTHER INFORMATION: Probe

<400> SEQUENCE: 28
tcgtcgtcgt cgtcgtcgtc gtcgtcgtcg tcgtcgtcg                            39

<210> SEQ ID NO 29
<211> LENGTH: 40
<212> TYPE: DNA
<213> ORGANISM: Artificial Sequence
<220> FEATURE:
<223> OTHER INFORMATION: Probe

<400> SEQUENCE: 29
ttcgttcgtt cgttcgttcg ttcgttcgtt cgttcgttcg                           40

<210> SEQ ID NO 30
<211> LENGTH: 40
<212> TYPE: DNA
<213> ORGANISM: Artificial Sequence
<220> FEATURE:
<223> OTHER INFORMATION: Probe

<400> SEQUENCE: 30
tagctagcta gctagctagc tagctagcta gctagctagc                           40

<210> SEQ ID NO 31
<211> LENGTH: 100
<212> TYPE: DNA
<213> ORGANISM: Artificial Sequence
<220> FEATURE:
<223> OTHER INFORMATION: Probe

<400> SEQUENCE: 31
ttttcttttc ttttcttttc ttttcttttc ttttcttttc cggtttaatc gtccggtcgt     60
agtggtgtct ccgccagcgc cgcaacctac gactcataca                          100

<210> SEQ ID NO 32
<211> LENGTH: 102
<212> TYPE: DNA
<213> ORGANISM: Artificial Sequence
<220> FEATURE:
<223> OTHER INFORMATION: Probe

<400> SEQUENCE: 32
ttccttttcc ttttcttttt cctttttcctt ttccttttcc ttcggtttaa tcgtccggtc    60
gtagtggtgt ctccgccagc gccgcaacct acgactcata ca                       102
```

```
<210> SEQ ID NO 33
<211> LENGTH: 54
<212> TYPE: DNA
<213> ORGANISM: Artificial Sequence
<220> FEATURE:
<223> OTHER INFORMATION: Probe

<400> SEQUENCE: 33
ttccttttcc ttttcctttt cctttcctt ttccttttcc ttttcctttt cctt          54

<210> SEQ ID NO 34
<211> LENGTH: 30
<212> TYPE: DNA
<213> ORGANISM: Artificial Sequence
<220> FEATURE:
<223> OTHER INFORMATION: Probe

<400> SEQUENCE: 34
ttccttttcc ttttcctttt cctttcctt                                      30

<210> SEQ ID NO 35
<211> LENGTH: 18
<212> TYPE: DNA
<213> ORGANISM: Artificial Sequence
<220> FEATURE:
<223> OTHER INFORMATION: Probe

<400> SEQUENCE: 35
ttccttttcc ttttcctt                                                  18
```